(12) United States Patent
Detty et al.

(10) Patent No.: US 6,984,656 B2
(45) Date of Patent: Jan. 10, 2006

(54) CORE MODIFIED PORPHYRINS

(75) Inventors: Michael R. Detty, Rochester, NY (US); Sandra O. Gollnick, Williamsville, NY (US); Sherry Davies, Buffalo, NY (US); Allan Oseroff, Buffalo, NY (US); Masako Abe, Buffalo, NY (US); David Hilmey, Columbus, OH (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 10/208,395

(22) Filed: Jul. 30, 2002

(65) Prior Publication Data

US 2003/0069219 A1 Apr. 10, 2003

Related U.S. Application Data

(60) Provisional application No. 60/308,616, filed on Jul. 30, 2001.

(51) Int. Cl.
*A61K 31/40* (2006.01)

(52) U.S. Cl. ............... 514/410; 514/422; 514/184; 540/145

(58) Field of Classification Search ............... 514/184, 514/410, 422, 115; 540/146, 145
See application file for complete search history.

(56) References Cited

PUBLICATIONS

Corey E. Stilts, Mariana I Nelen, David G. Hilmey, Sherry R. Davies, Sandra O. Gollnick, Allan R. Oseroff, Scott L. Gibson, Russell Hilf and Michael R. Detty; Water–Soluble, Core–Modified Porphyrins as Novel, Longer–Wavelength–Absorbing Sensitizers for Photodynamic Therapy, J. Med. Chem. 2000, 2403–2410 43, published on web May 26, 2000.

Ziolkowski et al. *5, 20–BIS (4–Sulphophenyl) –10, 15–BIS (2–Methoxy–4–Sulphophenyl) –21–Thiaporphyrin as a New Potent Sensitizer in Photodynamic Therapy*, Tumari, 1995, vol. 81, pp. 364–369.

*Primary Examiner*—Dwayne Jones
(74) *Attorney, Agent, or Firm*—Hodgson Russ LLP

(57) ABSTRACT

The present invention is directed to novel photosensitive compounds that can be replicated with great certainty and provide applications for photodynamic therapy.

15 Claims, 22 Drawing Sheets

1, X = S, Y = NH
2, X = Se, Y = NH
3, X = Y = S, Ar = $C_6H_5$
4, X = Y = Se, Ar = $C_6H_5$
5, X = S, Y = Te, Ar = $C_6H_5$
6, X = Y = S, Ar = $C_6H_4SO_3Na$
7, X = Y = Se, Ar = $C_6H_4SO_3Na$
TPPS$_4$, X = Y = NH, Ar = $C_6H_4SO_3Na$

DH-82, E = E' = S, X = F, Y = SO₃Na
10, E = S, E' = Se, X = F, Y = SO₃Na
11, E = Se, E' = S, X = F, Y = SO₃Na
DH-105, E = E' = Se, X = F, Y = SO₃Na
12, E = S, E' = NH, X = F, Y = SO₃Na
13, E = E' = S, X = CF₃, Y = SO₃Na
14, E = E' = S, X = NMe₂, Y = SO₃Na
15, E = E' = S, X = H, Y = OCH₂CO₂Na
MA-99, E = E' = S, X = F, Y = OCH₂CO₂Na

CORE MODIFIED PORPHYRINS

CLAIM OF PRIORITY

This application claims priority to U.S. provisional patent application No. 60/308,616, filed on Jul. 30, 2001.

FIELD OF THE INVENTION

The present invention is directed to photosensitive compounds.

BACKGROUND OF THE INVENTION

Photodynamic therapy (PDT) is a treatment regime that can better differentiate cancerous and normal tissue while minimizing or eliminating many of the side effects associated with conventional chemotherapy and radiation. PDT combines light and endogenous oxygen with a photosensitizer localized in or around the tumor. Irradiation of the sensitizer produces a cascade of biochemical events that kill cancer cells either directly or indirectly through the induction of vascular damage to blood vessels feeding the tumor or through induction of a host response. PDT has regulatory approval in the USA, Canada, The Netherlands, France, Germany, and Japan for cancers of the lung, digestive tract, and genitourinary tract using Photofrin® as a photosensitizer. PDT with Photofrin® is also being evaluated as a protocol for treating cancers of the head and neck region and for treating pancreatic cancer, as well as a possible therapy against Karposi's sarcoma, cancers of the brain, breast (both primary and metastatic), skin, and abdomen.

Photofrin® has been shown to be effective against a number of malignancies and has led to the acceptance of PDT in the clinic, but it is not the "ideal" photosensitizer. Photofrin® and most other porphyrin-related sensitizers have a weak absorbance in the red region of the spectrum ($\geq 630$ nm where penetration of light in tissue is optimal, FIG. 1). Photofrin® also induces long-lasting skin photosensitivity (2–3 months) due to retention of porphyrin moieties in cutaneous tissue.

Because Photofrin® is not a well-defined, single agent, it is difficult to modify chemically for investigation of structure/activity relationships. These limitations and the acceptance of PDT as a treatment protocol have stimulated research efforts toward the development of sensitizers for PDT that fit the definition of an ideal sensitizer as described below.

An ideal photosensitizer should have the following characteristics: (1) chemical purity and known composition, (2) toxicity only in the presence of light, (3) preferential retention in the target tissue, (4) rapid excretion following treatment, (5) low systemic toxicity, (6) high quantum yield for the photochemical process (high triplet yields, $\phi_T$, and long triplet lifetimes, $\tau_T$, to generate singlet oxygen and other reactive oxygen species), and (7) strong absorbance with a high extinction coefficient, $\epsilon$, in the 630–800 nm range where tissue penetration of light is at a maximum while still being energetic enough to produce singlet oxygen.

Different disease states may place entirely different requirements on the chemical and biological properties of the "ideal" sensitizer.

Based on Photofrin®'s success and acceptance as a clinical procedure, the next generation of porphyrin-related photosensitizers are currently being developed and evaluated in clinical trials. 5-Aminolevulinic acid (ALA)-induced generation of protoporphyrin IX, an effective PDT sensitizer, has received FDA approval for treatment of actinic keratosis and is in clinical trials for other conditions. However, ALA treatment is not as universal as exogenously administered porphyrins because different tissues produce different amounts of protoporphyrin IX.

Tetra(m-hydroxyphenyl)chlorin (mTHPC) and tin etiopurpurin (SnET2) absorb more strongly in the red region of the spectrum ($\lambda_{max}$ 652 nm, $\epsilon$=30,000 M$^{-1}$ cm$^{-1}$ for mTHPC; $\lambda_{max}$ 660 nm, $\epsilon$=28,000 M$^{-1}$ cm$^{-1}$ for SnET2) than Photofrin®, but still show undesirable skin photosensitization (up to 6 weeks after administration). Modifications of mTHPC (the preparation of polyethylene glycol/mTHPC conjugates) give an increase in tumor selectivity in a rat-liver tumor model and in a rat ovarian tumor model.

A benzoporphyrin derivative also absorbs strongly in the red region of the spectrum ($\lambda_{max}$ 690 nm, $\epsilon$=35,000 M$^{-1}$ cm$^{-}$), and shows limited skin photosensitivity (3–5 days), but is rapidly eliminated from all tissues including the tumor providing a narrow treatment window 0.5–2.5 h post-injection. However, the benzoporphyrin derivative (as Verteporfin®) has been approved for the treatment of age-related macular degeneration where the rapid clearance is desirable.

Other naturally occurring porphyrin-related molecules have also been evaluated as photosensitizers. The bacterio-chlorins have absorption maxima ($\lambda$ max) between 760 and 780 nm and have been studied as photosensitizers by several investigators, but are extremely sensitive to oxidation.

HPPH (the hexyl ether derivative of pyropheophorbide a) is currently in Phase I clinical trials for treating basal cell carcinoma and Barrett's esophagus and was developed following a structure-activity relationship (structure/activity relationship) study correlating lipophilicity with PDT efficacy in a series of pyropheophorbide a derivatives.

Texaphyrins are related to porphyrins in structure, but have five nitrogen atoms in the central core. Phase II clinical trials have just been completed with lutetium texaphyrin (Lu-Tex) as a photosensitizer for recurrent breast cancer and Phase I clinical trials are beginning using Lu-Tex for recurrent prostate cancer and cervical cancer. Lu-Tex has shown minimal skin photosensitivity due to rapid clearance, which leads to a fairly narrow treatment window 4–6 h post-injection. A major advantage to using Lu-Tex is its strong absorbance deeper in the red region of the spectrum ($\lambda_{max}$ 732 nm, $\epsilon$=42,000 M$^{-1}$ cm$^{-1}$) where tissue penetration of light is greater.

Gadolinium texaphyrin, where lutetium is replaced with gadolinium in the central core, has been developed as a radiation sensitizer to enhance radiation therapy. While results with the texaphyrins are optimistic, some concerns exist over their specificity, as well as pain during treatment.

Phthalocyanines and naphthalocyanines absorb even more strongly in the red region of the spectrum ($\lambda_{max}$ 670–780 nm, $\epsilon \geq 100,000$ M$^{-1}$ cm$^{-1}$) and are in the early stages of preclinical and clinical evaluation.

The later-generation photosensitizers are structurally similar to Photofrin® (all nitrogen heteroatoms in the core ring) and might be expected to have similar biological targets. The photodamage produced by PDT with porphyrin- and phthalocyanine-related materials appears to be from a combination of extracellular damage to vasculature and lymphatic structures and direct cell killing through both necrotic and apoptotic pathways with the mitochondria as an important target.

While current sensitizer research has provided several porphyrin-related photosensitizers with considerable promise, a single, "ideal" sensitizer has yet to emerge. With later-generation photosensitizers, it is very unlikely that a single photosensitizer will ever serve all the-diseases in oncology. Therefore, it is desirable to extend PDT into the treatment of other conditions and hence, the need to develop new photosensitizers with optimal properties for treating a given condition. The development of new photosensitizers with optimal properties for treating a given condition will depend upon an understanding of structure/activity relationships within the new class of photosensitizers and their applicability in general to other classes. PDT is a viable therapeutic approach not only for the treatment of cancer, but also for diverse other disease states including actinic keratosis, psoriasis, and age-related macular degeneration. PDT may also be clinically beneficial in other treatments such as blood purging, clot removal, and the removal of arterial plaque. The sensitizers for each of these applications may require quite different characteristics for optimal efficacy.

SUMMARY OF THE INVENTION

The present invention is directed to novel photosensitive compounds that can be replicated with great certainty and provide applications for photodynamic therapy.

DETAILED DESCRIPTION OF THE PRESENT INVENTION

The present invention is directed to a novel series of modified porphyrins as shown in the FIGS. 12, 12a, 12b, 13 and 14. These compounds are representative samples of the invention, and all are sensitizers for PDT. In particular, all these compounds have efficacy and other desirable properties: long-wavelength absorption maxima, high quantum yields for singlet oxygen generation, tumor selectivity with high cellular uptake, a high therapeutic index, and minimal skin photosensitization at a therapeutic dose.

Figure 12:
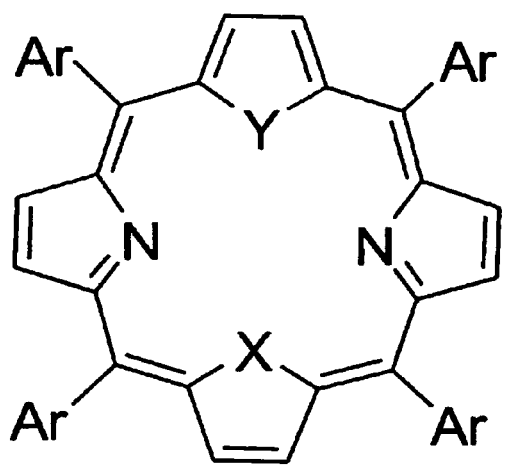
FIGS. 12, 12a, 12b, 13 and 14 illustrate the compounds of the present invention.
Figure 12A:
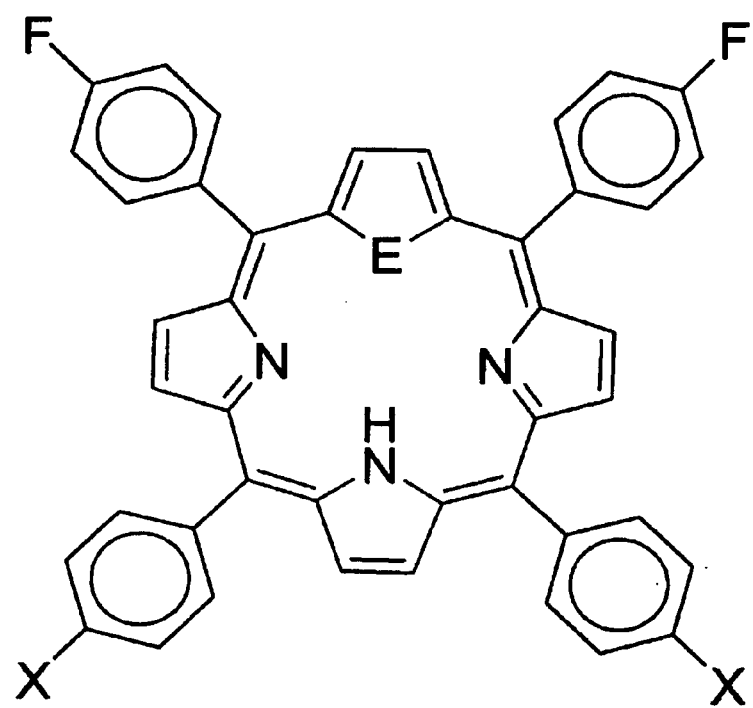
Figure 12B:
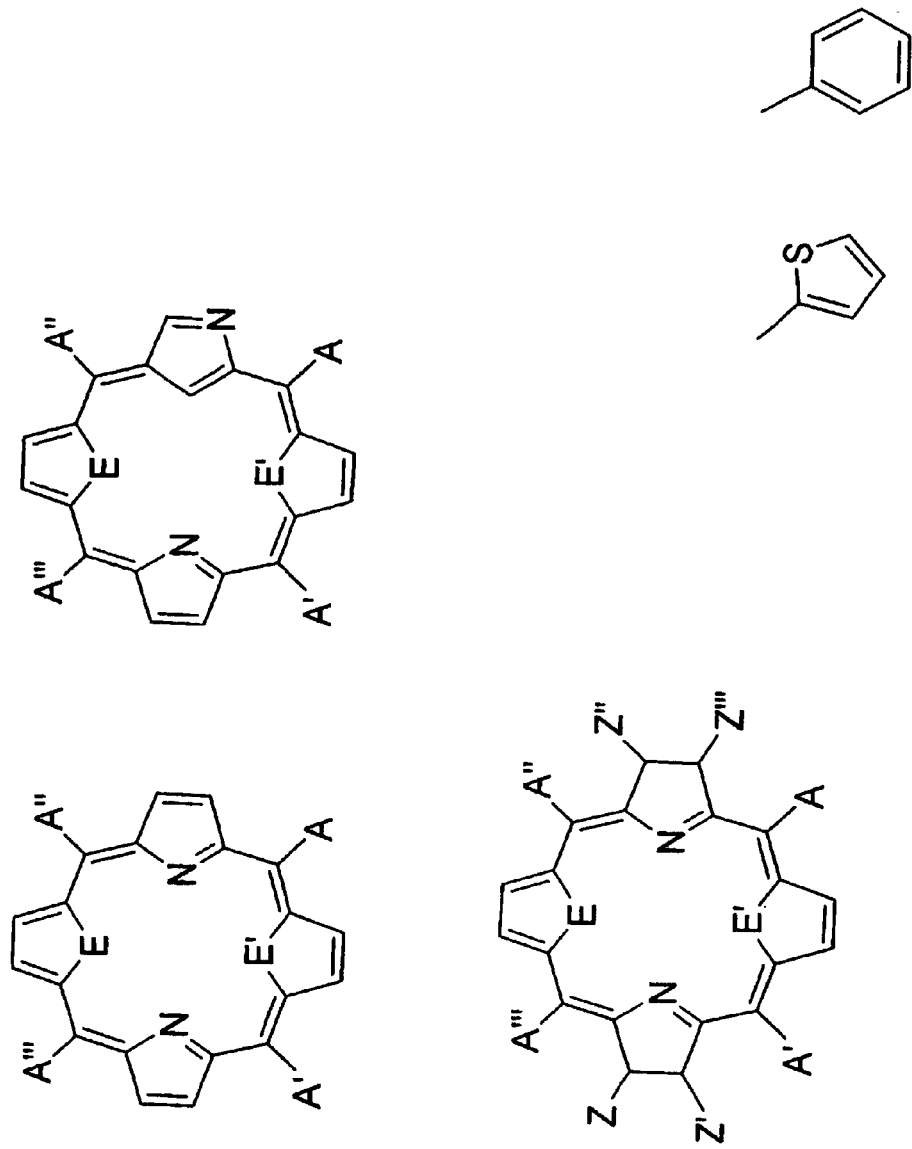
Figure 13:
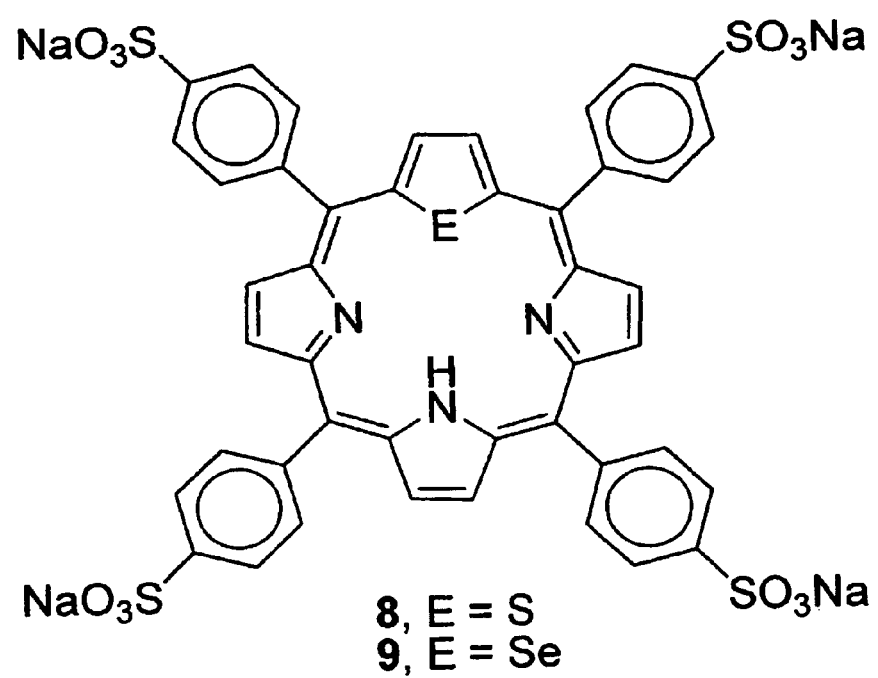

As detailed below, the different solubilizing groups and heteroatoms in DH-82, DH-105, and MA-99, identified in the FIGS. 12, 12a, 12 b, 13 or 14, impact efficacy and skin photosensitization. The biological activity of DH-82 and MA-99 in vitro was evaluated with respect to: 1) relative uptake and intracellular stability in cultured cells and 2) dark and light-induced toxicity of the photosensitizers toward cultured cells.

The activity of DH-82 and MA-99 (both shown in FIG. 12a) in isolated mitochondrial suspensions and in mitochondria in whole cells was evaluated to determine photosensitizer-induced inhibition of mitochondrial function. The pharmacodynamic influence of the host were evaluated in mitochondria obtained from DH-82- or MA-99-treated, tumor-bearing animals. Lysosomal localization in cells treated with DH-82 or MA-99 were determined. The pharmacokinetics of dye distribution and retention in cancerous and normal tissue were determined with DH-82 and MA-99. PDT with DH-82 and MA-99 in murine and rat tumor models were optimized by varying the sensitizer dose, the delivery vehicle, the interval between sensitizer administration and irradiation, fluence rate, fluence, and application of fractionated irradiation.

Synthetic routes were developed to prepare 21,23-dichalcogenaporphyrin photosensitizers for PDT that permit variation of substituents that impact biological properties. The two chalcogen of DH-82 and MA-99 atoms could be the same or different. Selected derivatives will be prepared to establish quantitative structure/activity relationships. The impact of substituent changes on absorption spectra in various solvents, solubility in various solvents, n-octanol/water partition coefficients, quantum yields for singlet oxygen generation, and quantum yields for one- and two-photon fluorescence were measured for these novel compounds. Photosensitizer solubility in potential delivery vehicles will also be determined. The effects of structural changes on physical and photophysical studies were combined with structure/activity relationship studies with respect to biological properties as described below. In a feedback cycle, chalcogen and other substituents were selected to enhance desirable chemical, photophysical, and biological properties for PDT.

The biological activity of the present invention of photosensitizers having appropriate absorption, chemical, and photophysical properties were evaluated in vitro and in vivo for DH-82 and MA-99.

Photofrin®, which is refined hematoporphyrin derivative, and protoporphyrin IX are complicated molecules to synthesize and structure/activity relationship studies of related derivatives of these molecules are stymied by this limitation. In contrast, 5,10,15,20-tetraaryl porphyrins can be prepared as single, well-characterized entities as either lipophilic or water-soluble photosensitizers. 5,10,15,20-Tetrakis (4-sulfonato-phenyl)porphyrin (TPPS$_4$, FIG. 12) has shown excellent membrane permeability and is one of the more selective porphyrins for accumulation in tumors with demonstrated efficacy both in vitro and in vivo. Analogues of TPPS$_4$ have been prepared and a limited structure/activity relationship was developed, which was shared by sulfonated phthalocyanines. The number and placement of solubilizing groups markedly affected biodistribution, localization, and efficacy in both classes. Two sulfonato groups on adjacent aromatic rings on either the phthalocyanine core or on the aryl substituents at the 5- and 10-positions of the porphyrin core provided optimal properties for uptake and biodistribution. While porphyrins in general have shown little toxicity, neurotoxicity in mice at high concentrations of TPPS$_4$ (150 mg/kg) in mice have hindered the clinical development of TPPS$_4$.

Figure 1:
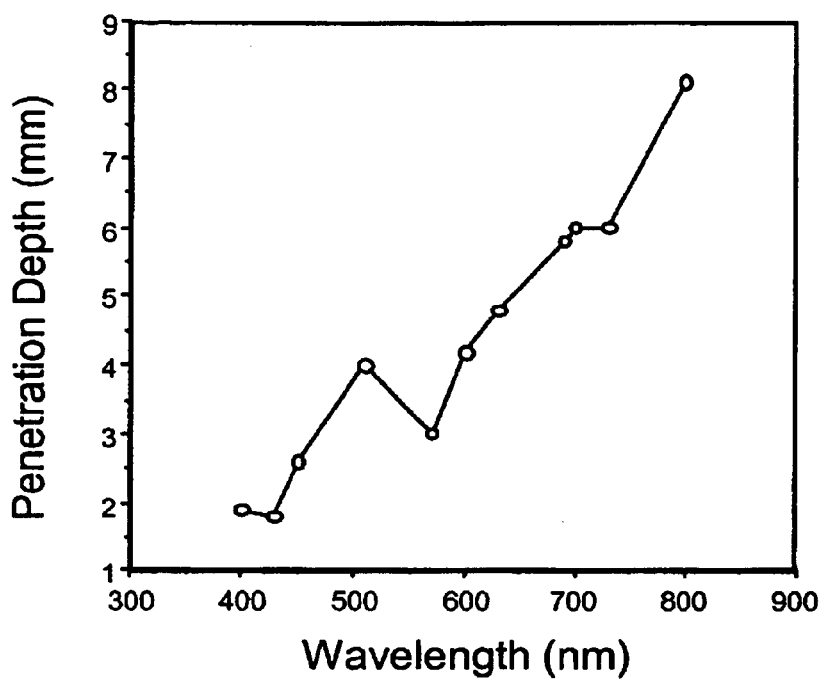
FIG. 1 is a graphical representation of the penetration of visible light at various wavelengths through bovine muscle.

The development of other porphyrins has been limited by the absorption maximum of the long-wavelength band. Like Photofrin®, TPPS$_4$ and related analogues have a band 1 absorption maximum near 630 nm. As shown in FIG. 1, light transmission through tissues roughly doubles between 550 nm and 630 nm, and roughly doubles again between 630 nm to 700 nm. An additional increase in tissue penetration is noted between 700 and 800 nm. Consequently, longer-wavelength-absorbing photosensitizers are advantageous by using wavelengths of light that penetrate more deeply into tumors.

Many variations of porphyrin-related molecules have been prepared and evaluated as photosensitizers for PDT. Most of these variations are subtle. Various meso-substituents have been incorporated in the porphyrin molecule to give longer wavelength absorption maxima. Chlorin and bacteriochlorin derivatives are the products of reduction of one or two pyrrole carbon-carbon double bonds, respectively. A more dramatic change is present in the texaphyrin derivatives, which have five nitrogen atoms in the central core.

A fundamentally different approach to longer-wavelength-absorbing porphyrins is to substitute other heteroatoms for one or two pyrrole nitrogen atoms in the core. Both 21- and 21,23-core-modified porphyrins containing the chalcogen atoms sulfur, selenium, and tellurium are part of the present invention (compounds 1–5, FIG. 12) and are characterized by longer wavelengths of absorption in band 1 ($\geq 650$ nm for 21-core-modified porphyrins and $\geq 695$ nm for 21,23-core modified porphyrins). Unlike any of the porphyrin, chlorin, bacteriochlorin, or texaphyrin derivatives, the 21,23-heteroatom contacts are less than the sum of Van der Waals' radii and the 21,23-core-modified porphyrins are no longer capable of binding a metal ion within the core and can only bind metals that approach the heteroatoms from above or below the porphyrin core. Furthermore, the core rings are somewhat puckered, which impacts the ability of the core-modified porphyrins to stack or aggregate. Thus, an structure/activity relationship study of porphyrin-related sensitizers, in which not only the meso-substituents but also the heteroatoms of the porphyrin core can be altered, were performed.

The chalcogen-for-nitrogen substitution does not hinder biological activity as a photosensitizer as exemplified by water-soluble analogues of 21-core-modified porphyrins 1 and 2 both in vitro and in vivo. Sulfonated 21-core-modified porphyrins 1 and were reported to be comparable to chlorin e$_6$ for efficacy in vivo with BFS1 sarcoma-bearing mice and no skin photosensitization was observed in animals irradiated 24 h post-injection of sulfonated 2.

Sulfonation of 21,23-dichalcogenaporphyrins 3 and 4 gave 5,10,15,20-tetrakis(4-sulfonatophenyl)-21,23-dithiaporphyrin (6, FIG. 12) and its 21,23-diselena analogue 7 (FIG. 12) as the tetrasodium salts. Sulfonation as a means to add water solubility has also worked well with other porphyrins and core-modified porphyrins. Both 6 and 7 have band 1 absorption maxima of 695 nm, which is significantly longer than the band 1 maximum of 630 nm for either Photofrin® or other tetraaryl porphyrins in water. Furthermore, both 6 and 7 are efficient generators of singlet oxygen with the quantum yield for singlet oxygen generation [$\phi(^1O_2)$] of 0.50 for 6 and 0.17 for 7 in aqueous solution.

Core-modified porphyrin 6 is phototoxic toward Colo-26 cells, a murine colon carcinoma cell line, in vitro with negligible dark toxicity at concentrations $\leq 100$ μg/mL ($\leq 100$ μM). In vivo, no toxicity, morbidity, or side effects were observed in BALB/c mice followed for 90 days post-injection of 10 mg (10 μmol)/kg of 6 under normal vivarium conditions (daily cycle of 12 h of fluorescent light/12 h of darkness). In BALB/c mice bearing either Colo-26 tumors or EMT-6 tumors (a murine mammary tumor), core-modified porphyrin 6 was preferentially taken up by tumor as measured by fluorescence from 6 and the fluorescence level was roughly linear with respect to dose.

Core-modified porphyrin 6 gave a PDT response in vivo with 694-nm light in BALB/c mice bearing Colo-26 tumors. Animals treated with photosensitizer 6 at 3.25 mg (3.0 μmol)/kg and light required 10.3±0.8 d to reach 400-mm$^3$ tumor volume, which was more than double the time for control animals (4.3±1.0 d) receiving neither drug nor light (P <0.01). The delay in tumor growth was also significantly greater than that observed for animals treated with TPPS$_4$ (6.7±1.1 d at 10 mg/kg, P <0.014).

Based on the efficacy observed with 6, the clearance of photosensitizer 6 using the murine ear swelling protocol has been used with Photofrin® and other porphyrin-related sensitizers. BALB/c mice were treated with 5 mg/kg of photosensitizer 6 and the ear-swelling response (ESR) was determined at selected time-points. The ESR disappeared completely between 14 and 21 days post-injection. With Photofrin, ® a measurable ESR was still observed at 31 days post-injection. Fluorescence measurements were used to monitor clearance from the serum, which indicated that 6 had cleared the serum after 7 days while clearance from the serum was not observed with Photofrin® until 21 days post-injection.

Photosensitizers DH-82, DH-105, and MA-99 are exciting compounds for core-modified porphyrins as PDT sensitizers. All these photosensitizers are readily prepared and purified by a synthetic route amenable to the preparation of diverse other derivatives. These compounds and related 21,23-dichalcogenaporphyrins have well-defined chemical structures and can be prepared as pure, single compounds. All the present photosensitizers have a high quantum yield for singlet-oxygen generation [$\phi(^1O_2)$ >0.7 in aqueous solution], are water-soluble for easy administration into patients, have a band I absorption maximum that is further to the red (701 nm for DH-82, 703 nm for DH-105, and 717 nm for MA-99) than Photofrin® (630 nm), which allows wavelengths of light to be used that penetrate more deeply into tissue (see FIG. 1). Both DH-82 and MA-99 show reduced photobleaching relative to Photofrin®, which may be a consequence of the puckered ring structure of the 21,23-core-modified porphyrins. DH-82, DH-105, and MA-99 show potency as photosensitizers against Colo-26 and R3230AC cell lines in vitro, as well as potency as a photosensitizer against Colo-26 tumors in BALB/c mice in vivo. Furthermore, all these photosensitizers have minimal skin photosensitization at therapeutic doses.

This invention defines the structure-activity relationships that characterize core-modified porphyrins and the results of these studies to the design and synthesis of photosensitizers with specific properties that match the requirements for PDT of different disease states. The substitution of chalcogen atoms for nitrogen in the core gives chromophores with absorption maxima at significantly longer wavelengths without damaging other desirable photophysical properties (extinction coefficient, singlet oxygen yield). This invention also illustrates the effects of chalcogen atom substitution in the core, substitution at the 5-, 10-, 15-, and 20-positions (the meso-positions), and solubilizing groups on biological properties such as the uptake, retention, selectivity, and clearance of the photosensitizer as well as the effects of substitution on efficacy both in vitro and in vivo. The data below demonstrates that chemical modification of core-modified porphyrins gives photosensitizers with significantly greater phototoxicity, efficacy, and with minimal skin photosensitization.

5,10,15,20-Tetraaryl Core-Modified Porphyrins.

The topological and chemical properties of dichalcogenaporphyrins impart unexpected biological properties relative to the corresponding porphyrin derivatives. 5,10,15,20-tetrakis(4-sulfonatophenyl)-21-thiaporphyrin 8 and 21-selenaporphyrin 9 (FIG. 13) were prepared and evaluated the phototoxicity in two tumor cell lines in vitro. Neither 21-core-modified porphyrin displayed significant phototoxicity, in marked contrast to the phototoxicity observed with 6.

Figure 14:
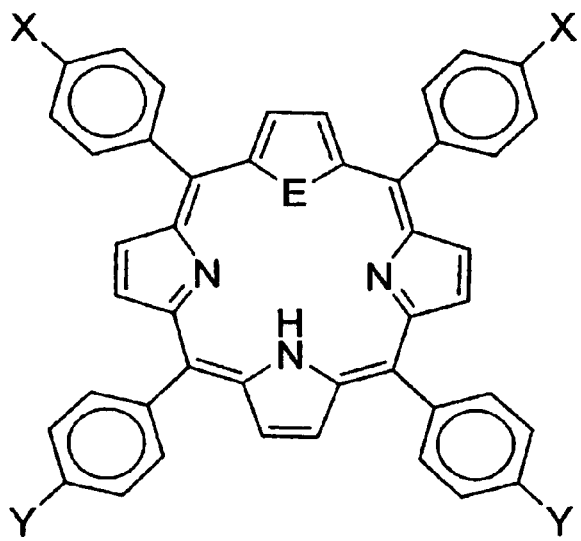

Analogues of core-modified porphyrin 6 are easily prepared, which greatly facilitates the design of a molecular series to elucidate structure-activity relationships. We synthesized a series of 5,10-bis(4-sulfonatoaryl)-15, 20-bis(aryl)-21,23- and 5,10-bis(4-carboxylatomethoxyphenyl)-15, 20-bisaryl-21,23-dichalcogenaporphyrins as illustrated in FIG. 14. The core-modified porphyrins were isolated as crystalline, single isomers (>98.5% purity by $^1$H and $^{13}$C NMR and HPLC). The absorption properties of this series are compiled in Table 1 below along with the quantum yields for the generation of singlet oxygen [$\phi(^1O_2)$]. Table 1. UV-visible band maxima and extinction coefficients [$\phi_{max}$ nm($\epsilon \times 10^{-3}$ M$^{-1}$ cm$^{-1}$)] in water, quantum yields for the generation of singlet oxygen [$\phi(^1O_2)$], and effective concentrations to give 50% cell-kill of Colo-26 cells in vitro with 4 J cm$^{-2}$ of light (EC$_{50}$) for TPPS$_4$ and core-modified porphyrins 6–8, 10–15, DH-82, DH-105, and MA-99.

some control over band I ($\lambda_{max}$ of 666–717 nm in these examples). These features are all positive attributes for sensitizers for PDT and suggest that structural modifications can be made to fine tune biological properties while maintaining desirable chemical and photophysical properties.

Figure 2:
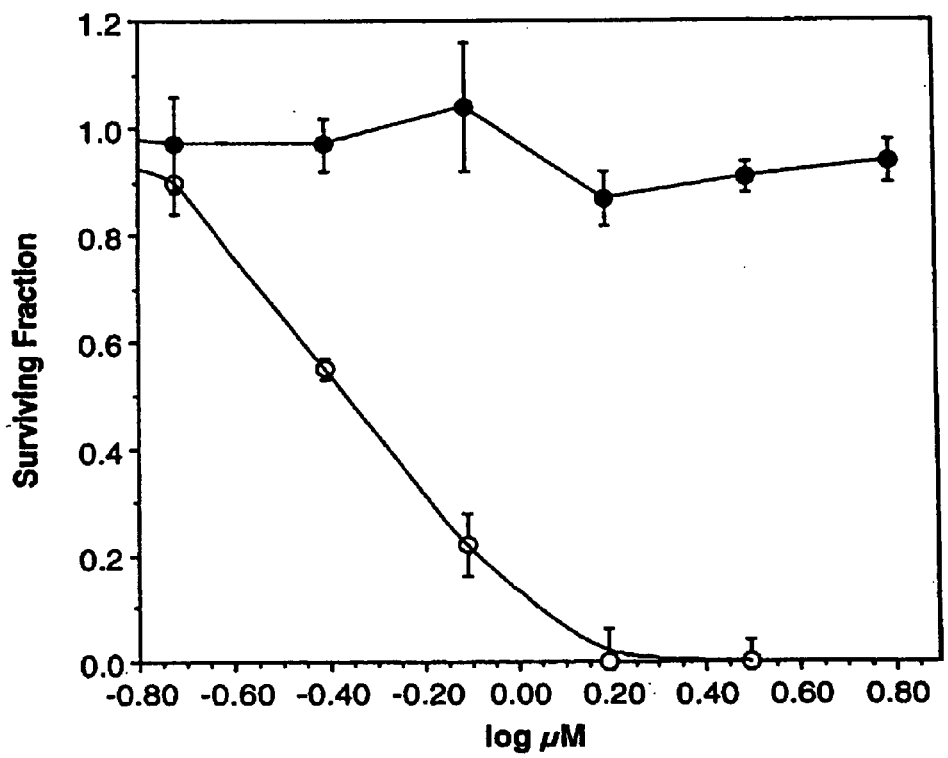
FIG. 2 is a graphical representation of the dark toxicity and the phototoxicity of MA-99 toward Colo-26 cells in culture.

In order to compare relative phototoxicity, the core-modified porphyrins of Table 1 were evaluated in culture for dark and light-induced toxicities toward Colo-26 cells, a murine colon carcinoma cell line. Cell cultures were incubated for 24 h in the dark with various concentrations of sensitizer and were then washed prior to treatment with filtered 590–800 nm light for a total light dose of 4 J cm$^{-2}$. Light-treated cells and dark controls were incubated for 24 h and cell survival was determined. Results are compiled in Table 1 as the effective concentration of sensitizer to give 50% cell kill with 4 J cm$^{-2}$ of 590–800 nm light (EC$_{50}$). Values of EC$_{50}$ were determined from a plot of the surviving fraction of cells vs. concentration of sensitizer as illustrated in FIG. 2 for MA-99. None of the core-modified porphyrins of Table 1 displayed significant dark toxicity at concentrations $\leq$50 $\mu$M.

In the 15,20-bis(4-sulfonatophenyl) series, compound 13, with lipophilic trifluoromethylphenyl groups at the 5- and 10-positions, displayed little phototoxicity. The fluoro substituents in 10–12, DH-82, and DH-105 and the dimethylanilino substituents in 14 are hydrogen-bond acceptors and the compounds containing them are more phototoxic than tetrasulfonates 6–8. Compound 15 and MA-99 with two carboxylate solubilizing groups have lower values of EC$_{50}$ than 10–12, 14, DH-82, and DH-105 with two 4-sulfonatophenyl solubilizing groups. From this information it is easy to design and compare photosensitizers containing various lipophilic, hydrogen-bond accepting, and solubilizing substituents. That the periphery of the porphyrin is important as well as the core in the determination of properties is illustrated by a comparison of 10–12, DH-82, and DH-105. The value of EC$_{50}$ for the 21-thiaporphyrin 12 is comparable to values of EC$_{50}$ for the core modified porphyrins 10, 11, DH-82, and DH-105 with identical 5,10-bis(4-fluorophenyl) and 15,20-bis(4-sulfonato-phenyl) substituents. In the evaluation of the core-modified porphyrin sensitizers, there also appears to be no correlation between EC$_{50}$ and quantum yields for the generation of singlet oxygen [$\phi(^1O_2)$].

| Compd | Soret | Band IV | Band III | Band II | Band III | $\phi$ ($^1O_2$) | EC50, $\mu$m |
|---|---|---|---|---|---|---|---|
| TPPS$_4$ | 411(464 | 513(15.5) | 549(7.0) | 577(6.5) | 630(3.9) | 0.71$^b$ | 125 |
| 6 | 434(190) | 513(19.3) | 546(5.5) | 633(2.0) | 695(4.0) | 0.50$^d$ | 30 |
| 7 | 434(221) | 513(22.4) | 546(6.2) | 631(2.2) | 695(4.5) | 0.17$^d$ | >100 |
| 8 | 425(445) | 515(22.4) | 550(7.2) | 607(4.0) | 666(4.2) | 0.80 ± 0.02 | >100 |
| DH-82 | 431(476) | 518(15.7) | 560(8.3) | 633(2.3) | 701(4.6) | 0.74 ± 0.03 | 1.6 |
| 10 | 437(443) | 515(34.9) | 549(10.8) | 634(2.6) | 698(7.1) | 0.65 ± 0.01 | 2.1 |
| 11 | 435(243) | 529(20.4) | 569(10.5) | 635(3.6) | 702(6.3) | 0.64 ± 0.01 | 1.2 |
| DH-105 | 439(65) | 538(10.3) | 580(5.1) | 634(3.0) | 703(3.8) | 0.55 ± 0.02 | 7.9 |
| 12 | 432(224) | 527(12.6) | 566(5.4) | 627(2.5) | 691(3.2) | 0.78 ± 0.05 | 2.1 |
| 13 | 440(270) | 524(19.7) | 559(7.0) | 637(2.1) | 701(4.2) | — | >100 |
| 14 | 428(79.7) 447(81.5) | 515(18.3) | 577(16.0) | 635(3.1) | 716(7.5) | 0.60 ± 0.02 | 0.6 |
| 15 | 434(234) | 514(21.6) | 549(9.9) | 634(1.7) | 699(5.6) | — | 0.15 |
| MA-99 | 442(127) | 533(14.0) | 573(10.8) | 645(2.5) | 717(4.8) | 0.71 ± 0.02 | 0.43 |

The compounds of Table 1 share some common characteristics: (1) all are soluble in water for ease of formulation and administration into patients ($\approx$10 mg/mL for sulfonates; $\approx$1 mg/mL for carboxylates), (2) all are efficient generators of singlet oxygen, and (3) all have absorption maxima at longer wavelengths than either of the porphyrin derivatives TPPS$_4$ or Photofrin®. However, substituent choices give Comparison of Core-Modified Porphyrins with Photofrin® and the HPPH in Vitro.

Figure 3:
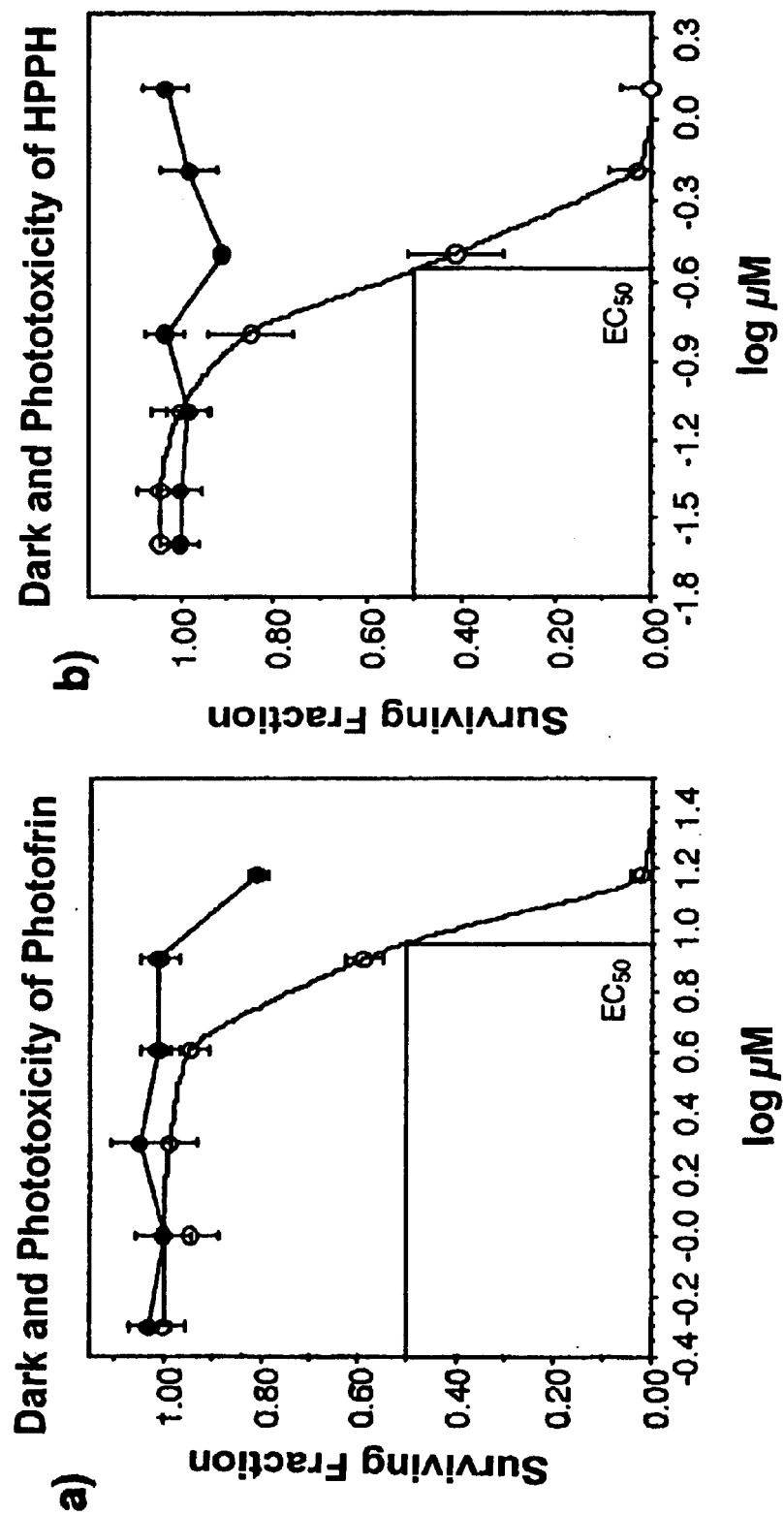
FIGS. 3a and 3b are graphical representation of the dark toxicity and phototoxicity of Photofrin® and HPPH, respectively, toward Colo-26 cells in culture.
Figure 4B:
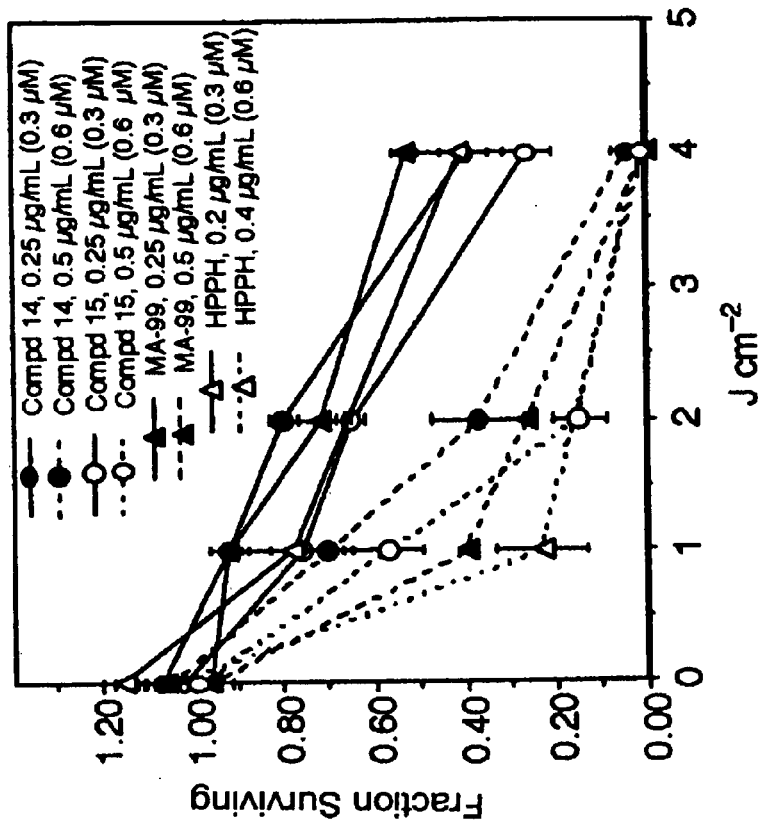
FIGS. 4a and 4b are comparison charts of the photosensitization of the particular compounds on the cell viability of cultured Colo-26 tumor cells.
Figure 4A:
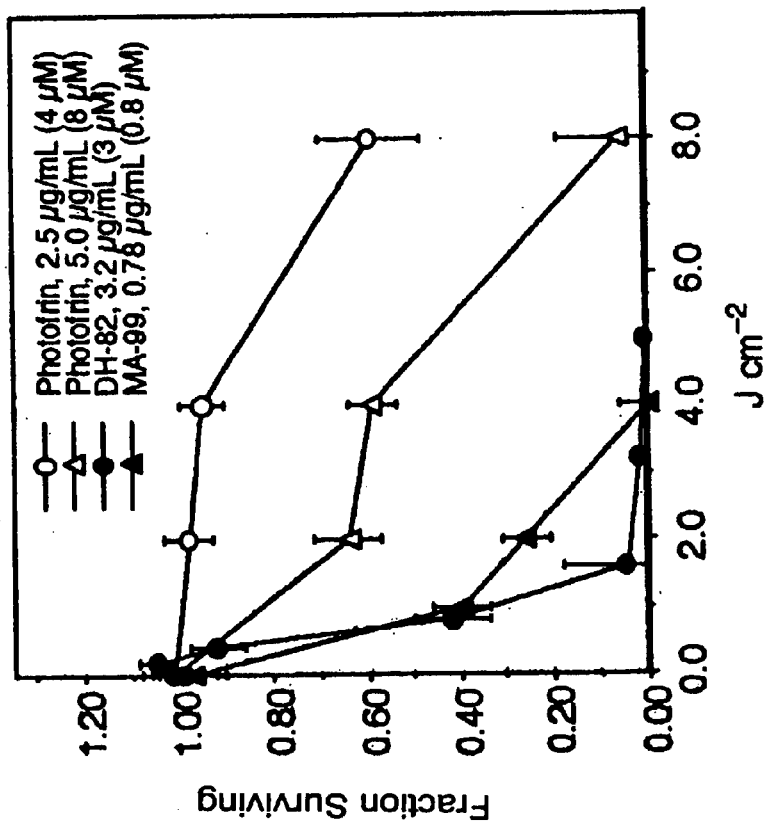

Photofrin®, in spite of its limitations, has been the workhorse photosensitizer in the lab and in the clinic. It should be noted that HPPH has been found to be superior to chlorin e$_6$ in efficacy and is a second-generation photosensitizer currently in clinical trial. Values of $EC_{50}$ against Colo-26 cells with 4 J cm$^{-2}$ of 590–800 nm light were determined for both Photofrin® and HPPH in vitro (for Photofrin®: $EC_{50}$ =9 μM, FIG. 3a; for HPPH: $EC_{50}$ =0.3 μM, FIG. 3b). Core-modified porphyrins 10–12, 14, 15, DH-82, DH-105, and MA-99 of Table 1 have $EC_{50}$ values that are lower than that of Photofrin® using filtered 590–800 nm light. As shown in FIG. 4a, both DH-82 and MA-99 show significantly greater phototoxicity at lower concentrations than Photofrin® using a 694 nm dye laser for excitation of DH-82 and MA-99 and a 630 nm dye laser for excitation of Photofrin, ® conditions that would more closely approximate a clinical light source. The $EC_{50}$ value for HPPH at 0.3 μM is 30-fold lower than for Photofrin®. Photosensitizers 14, 15, and MA-99 also have submicromolar values of $EC_{50}$ (Table 1) and have phototoxicities that are comparable to HPPH at similar concentrations as shown in FIG. 4b.

Figure 4C:
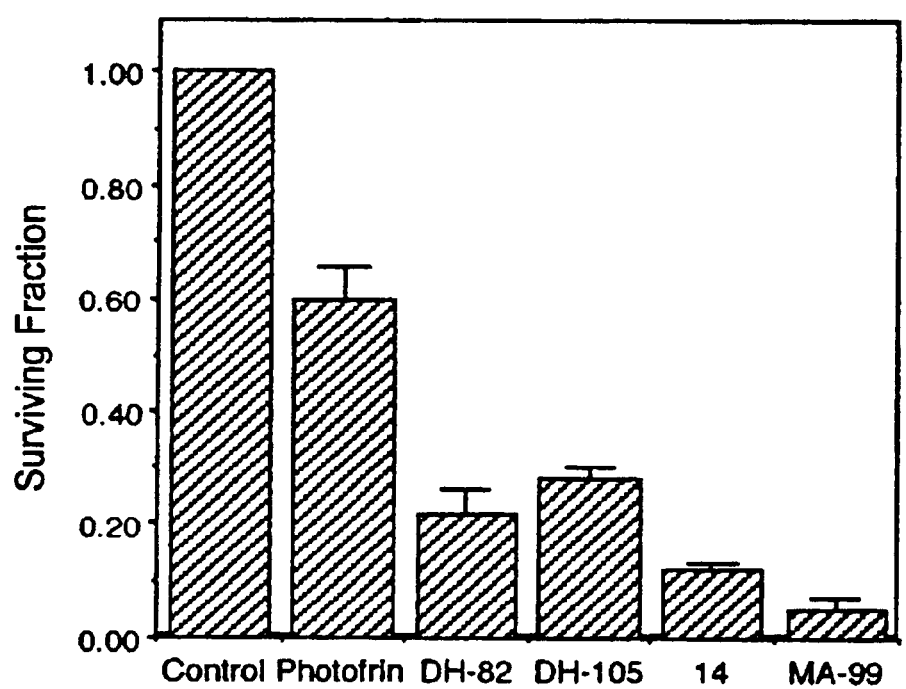
FIG. 4c is a graphical representation of the phototoxicity of Photofrin® and various photosensitizers toward R3230AC rat mammary adenocarcinoma cells in culture.

The relative phototoxicity of Photofrin®, DH-82, DH-105, photosensitizer 14, and MA-99 were also compared in a second cell line. Similar results were obtained with R3230AC rat mammary adenocarcinoma cells in vitro. Cell cultures were incubated for 24 h in the dark with 10 μM concentrations of Photofrin®, DH-82, DH-105, 14, or MA-99 and were then washed prior to treatment with filtered 570–800 nm light for a total light dose of 0.9 J cm$^{-2}$. Light-treated cells and dark controls were incubated for 24 h and cell survival was determined. The surviving fraction, 24 h post-irradiation, is shown graphically in FIG. 4c. As observed with Colo-26 cells (Table 1), DH-82, DH-105, photosensitizer 14, and MA-99 were all more phototoxic than Photofrin® against R3230AC cells. Furthermore, compounds 14 and MA-99 are more phototoxic than DH-82 and DH-105 toward R3230AC cells, which is analogous to their behavior against Colo-26 cells (Table 1).

Photobleaching of 21,23-Core-Modified Porphyrins and Photofrin.®

Figure 5:
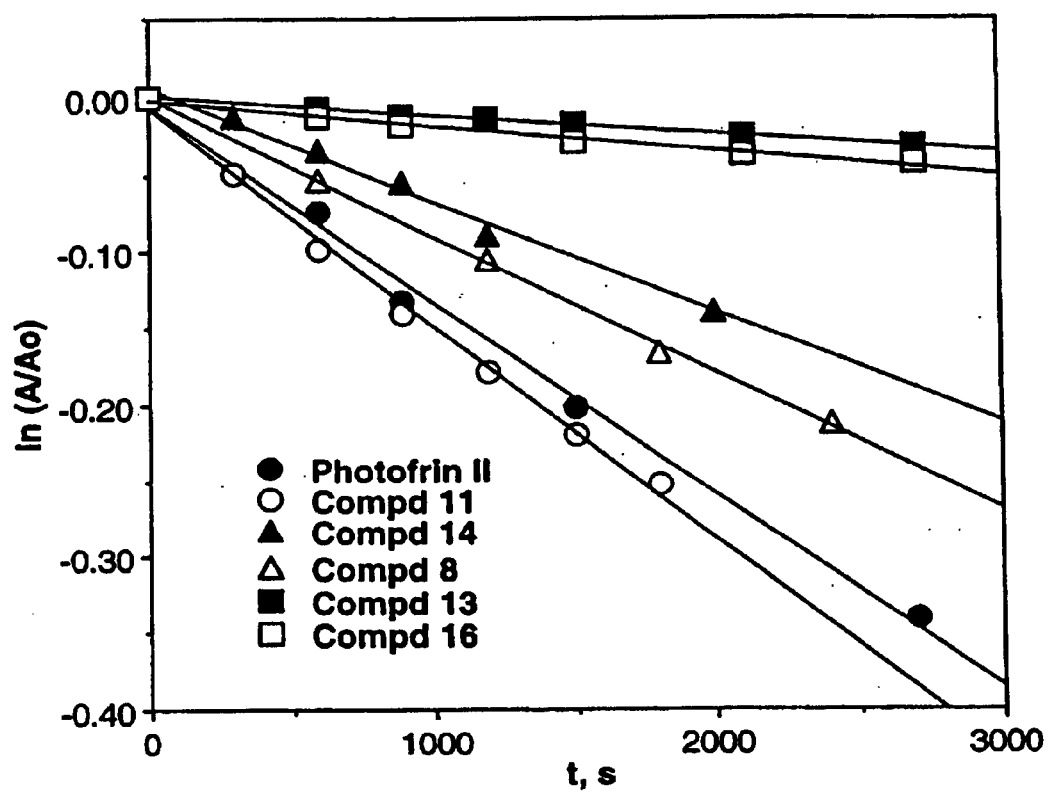
FIG. 5 is a graphical representation of photobleaching of Photofrin® and various core modified porphyrins.

One limitation of PDT dosimetry is the rate of photobleaching of the photosensitizer, which can be problematic with Photofrin® and even more problematic with the bacteriochlorins and the chlorins (such as HPPH). Rates of photobleaching of 21-core-modified porphyrin 12 and core-modified porphyrins 6, 7, 13–15, DH-82, DH-105, and MA-99 in phosphate-buffered saline (PBS) under conditions of constant initial absorbance between 570 and 750 nm using 570–750 nm light at 500 mW cm$^{-2}$ are compiled in Table 2 below and can be compared to that for Photofrin® as shown in FIG. 5 for several of these compounds.

TABLE 2 rate of photobleaching ($k_{bleach}$), emission maxima ($\lambda_F$), and quantum yield for fluorescence ($\phi_F$) for selected core-modified porphyrins.

| Compd | $K_{bleach}$, × $10^4$ s$^{-1}$ | $\lambda_F$, nm | $\phi_F$ (± σ) |
|---|---|---|---|
| Photofrin © | 1.27 ± 0.01 | — | — |
| TPPS$_4$ | — | — | 0.12$^c$ |
| 6 | 0.84 ± 0.02 | 700 | 8.6 (± 0.4) × 10$^{-3}$ |
| 7 | — | 700 | 8.9 (± 0.4) × 10$^{-4}$ |
| DH-82 | 0.85 ± 0.03 | 703 | 6.9 (± 1.1) × 10$^{-3}$ |
| 10 | — | 700 | 1.4 (± 0.1) × 10$^{-4}$ |
| DH-105 | 1.44 ± 0.03 | — | <10$^{-4}$ |
| 12 | 2.4 ± 0.2 | — | — |
| 13 | 0.13 ± 0.02 | 697 | 8.8 (± 0.8) × 10$^{-3}$ |
| 14 | 0.77 ± 0.04 | — | <10$^{-4}$ |
| 15 | 0.18 ± 0.02 | — | — |
| MA-99 | 0.16 ± 0.02 | 703 | 3.2 (± 0.1) × 10$^{-3}$ |

Photobleaching of thiaporphyrin 12 is more rapid than photobleaching of Photofrin® while photobleaching of diselenaporphyrin DH-105 is comparable in rate to the photobleaching of Photofrin®. While dithiaporphyrins 6, 14, and DH-82 are measurably slower to photobleach than Photofrin® dithiaporphyrins 13, 15, and MA-99 are nearly an order of magnitude more photostable in comparison to Photofrin®.

Single-Photon Quantum Yields for Fluorescence.

Figure 6:
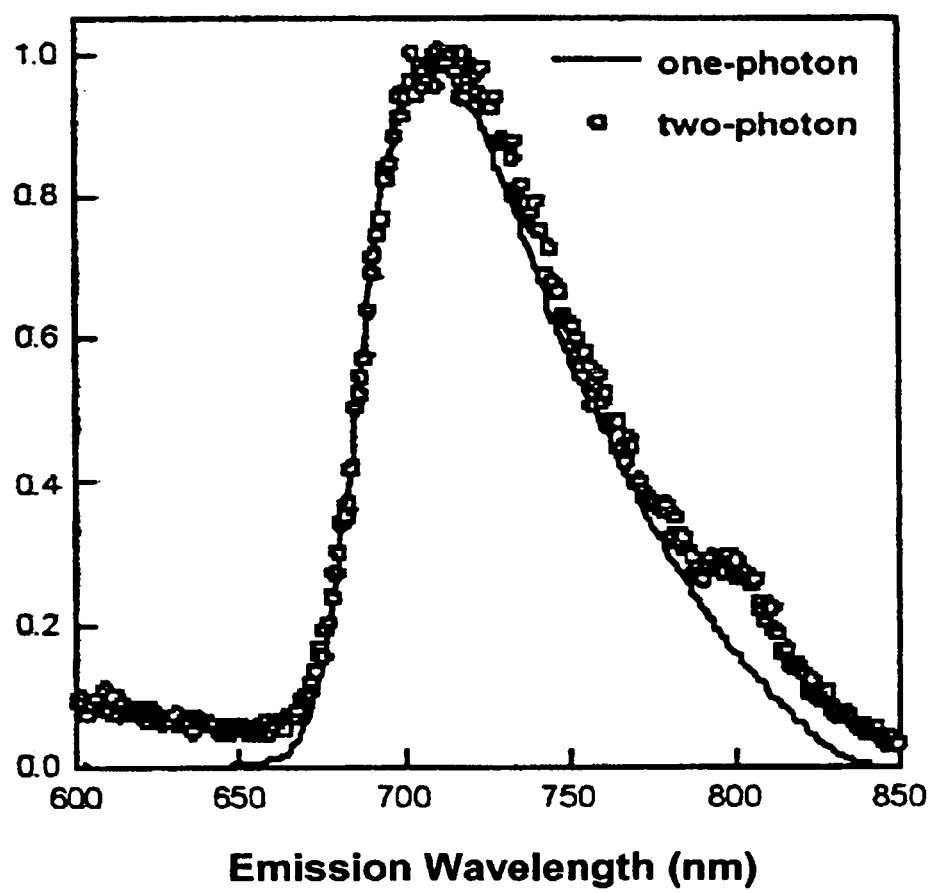
FIG. 6 is a graphical representation of one and two photon emission spectra for MA-99.

In vivo fluorescence techniques have had significant impact on the development of PDT with respect to the pharmacokinetics of sensitizers and to PDT dosimetry. Photofrin® has been used in fluorescent diagnostics and the fluorescence of TPPS$_4$ has been extensively studied. Several of the core-modified porphyrins of this invention were emissive (Table 2) and a typical one-photon emission spectra is shown in FIG. 6 for MA-99. A small (≦10 nm) Stokes shift is observed for the core-modified porphyrins. The quantum yield standard used in these studies was a freshly prepared solution of TPPS$_4$ ($\phi_F$ =0.12) dissolved in water. Photosensitizers 6, 13, and DH-82 have values of $\phi_F$ of just under 0.01 and photosensitizer MA-99 has a value of $\phi_F$ of 0.003. While these values of $\phi_F$ are low, the fluorescence is sufficient to facilitate measurements of tissue distribution and to be detectable in whole cells as described in the biological results below.

The introduction of selenium into the porphyrin core greatly reduces the quantum yield for fluorescence due to heavy atom effects. Diselenaporphyrin 7 is 10% as emissive as its dithiaporphyrin analogue 6. Thiaselenaporphyrin 10 is 2% as emissive as its dithiaporphyrin analogue DH-82 while diselenaporphyrin DH-105 gave no detectable emission.

Two-Photon Excitation of Core-Modified Porphyrins.

There has been an increasing interest in the two-photon excitation of photosensitizers used in PDT both for both therapeutic and diagnostic applications. Early attempts to use two-photon excitation in therapy with pyropheophorbide-a failed due to hyperthermia induced by the one-photon absorption of water of the 1060 nm light emitted from the Nd:YAG laser used. The use of near-infrared lasers emitting between 700 and 900 nm for two-photon excitation allows for deeper penetration of light and minimizes out of focus damage from one-photon absorption. The small focal volume of two-photon excitation is on the order of 1 μm$^3$, which is a volume smaller than most cells, which would permit either PDT or imaging at the subcellular level.

As shown in Table 1, the core-modified porphyrins have a strong absorption into the Soret band at around 430 nm, which is ideally suited for two-photon excitation with the Ti-sapphire laser at 900 nm. Several of the 21,23-dithiaporphyrins exhibited two-photon excitation with a Ti-sapphire laser at 900 nm using 100-fs pulses with a frequency of 76 MHz as illustrated in FIG. 6. The emission spectrum for MA-99 in FIG. 6 was collected from 650 to 850 nm following two-photon excitation. The two-photon emission spectra are essentially superimposable on the one-photon emission spectra as shown in FIG. 6, which indicates the same excited state for one- and two-photon processes. The two-photon absorption cross sections for compounds 13, DH-82, and MA-99 are on the order of 10$^{-50}$–10$^{-51}$ cm$^4$ s photon$^{-1}$ and are comparable to values determined for protoporphyrin IX. As described below, the two-photon excitation of the core-modified porphyrins are used to examine cellular sites of localization using two-photon confocal microscopy.

Distribution Studies in Vitro. A. Cellular Uptake and Intracellular Concentrations.

Figure 7:
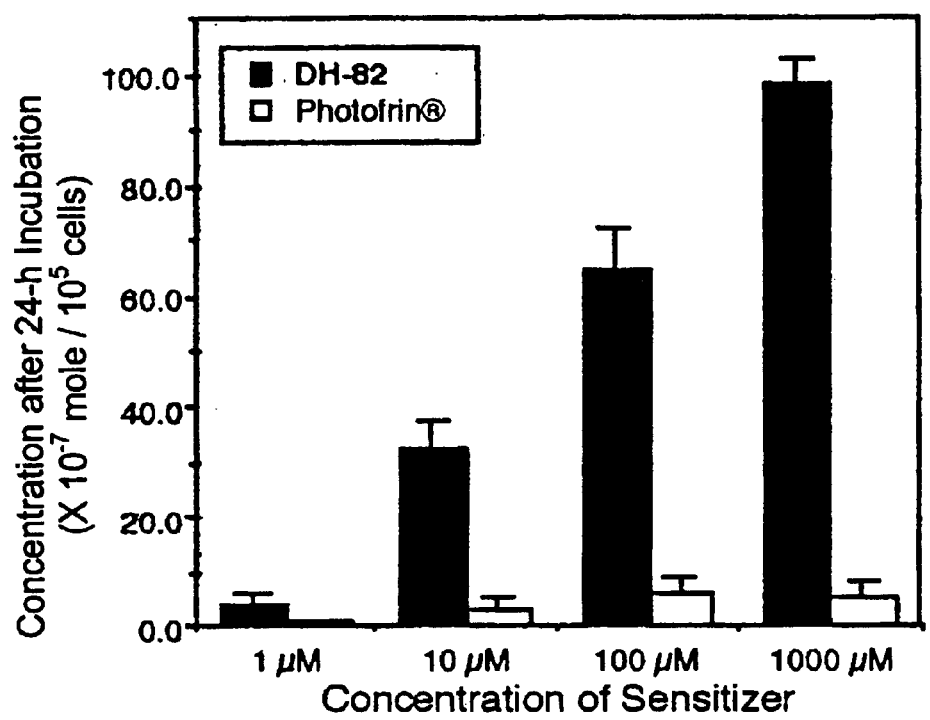
FIG. 7 is a graphical representation of the uptake of certain compounds in cells.

The greater phototoxicity of DH-82, MA-99, and other core-modified porphyrins relative to Photofrin® could be due to better photophysical properties such as a higher quantum yield for singlet-oxygen generation in cells. Alternatively, increased cellular uptake of the photosensitizer leads to greater phototoxicity. The uptake of DH-82 was compared to that of Photofrin® in cells in culture using photosensitizer fluorescence to determine intracellular concentrations (FIG. 7).

For photosensitizer uptake experiments, cultured MCF-7 cells were treated with solutions of either DH-82 or Photofrin® in minimal essential medium (MEM) at $1 \times 10^{-6}$ to $1 \times 10^{-3}$ M (1–1000 $\mu$M). To establish baseline fluorescence, control cells incubated with MEM not containing either photosensitizer were used. At 1, 3, 6, or 24 h after sensitizer addition, the sensitizer-containing medium was removed and the fluorescence of the cells was determined using excitation at 438 nm for DH-82 with the emission detected at 706 nm and excitation at 365 nm for Photofrin® with its emission detected at 630 nm. A time course to determine when the fluorescence approached its maximum was performed for DH-82 and Photofrin®. DH-82 required approximately 1 h to reach half of its maximum intracellular concentration while Photofrin® required approximately 5 h.

To determine the final intracellular concentrations of each sensitizer, cells in 96-well plates were incubated with sensitizer for 24 h. Detection of fluorescence in sensitizer-treated cells was made directly in the wells of the 96-well plate using the appropriate excitation and emission wavelengths. (Data are expressed as moles of sensitizer/$10^5$ cells.) Based on fluorescence, the final intracellular concentration of DH-82 was approximately ten times that of Photofrin® as shown in FIG. 7 at all extracellular concentrations of sensitizer. Comparable results were obtained with MA-99 at 10 $\mu$M and 100 $\mu$M where the final intracellular concentration was approximately 80% that for DH-82. As described above for phototoxicities in vitro, the $EC_{50}$ value for Photofrin® is 9.0 $\mu$M while $EC_{50}$ for DH-82 is 1.6 $\mu$M and for MA-99, 0.43 $\mu$M. The lower values of $EC_{50}$ for DH-82 and MA-99 relative to Photofrin® are not inconsistent with a higher cellular uptake. If such differences were maintained in vivo, then treatment doses with DH-82, MA-99, and related compounds could be significantly lower while maintaining efficacy. In fact as described below, our initial PDT results in tumor-bearing mice indicate that Photofrin® at 2.5 mg/kg, DH-82 at 0.13 mg (0.13 $\mu$mol)/kg, and MA-99 at 0.15 mg (0.19 $\mu$mol)/kg are comparable in efficacy. This again is consistent with higher cellular uptake of DH-82 and MA-99.

Effects on Cellular Cytochrome c Oxidase.

Figure 8:
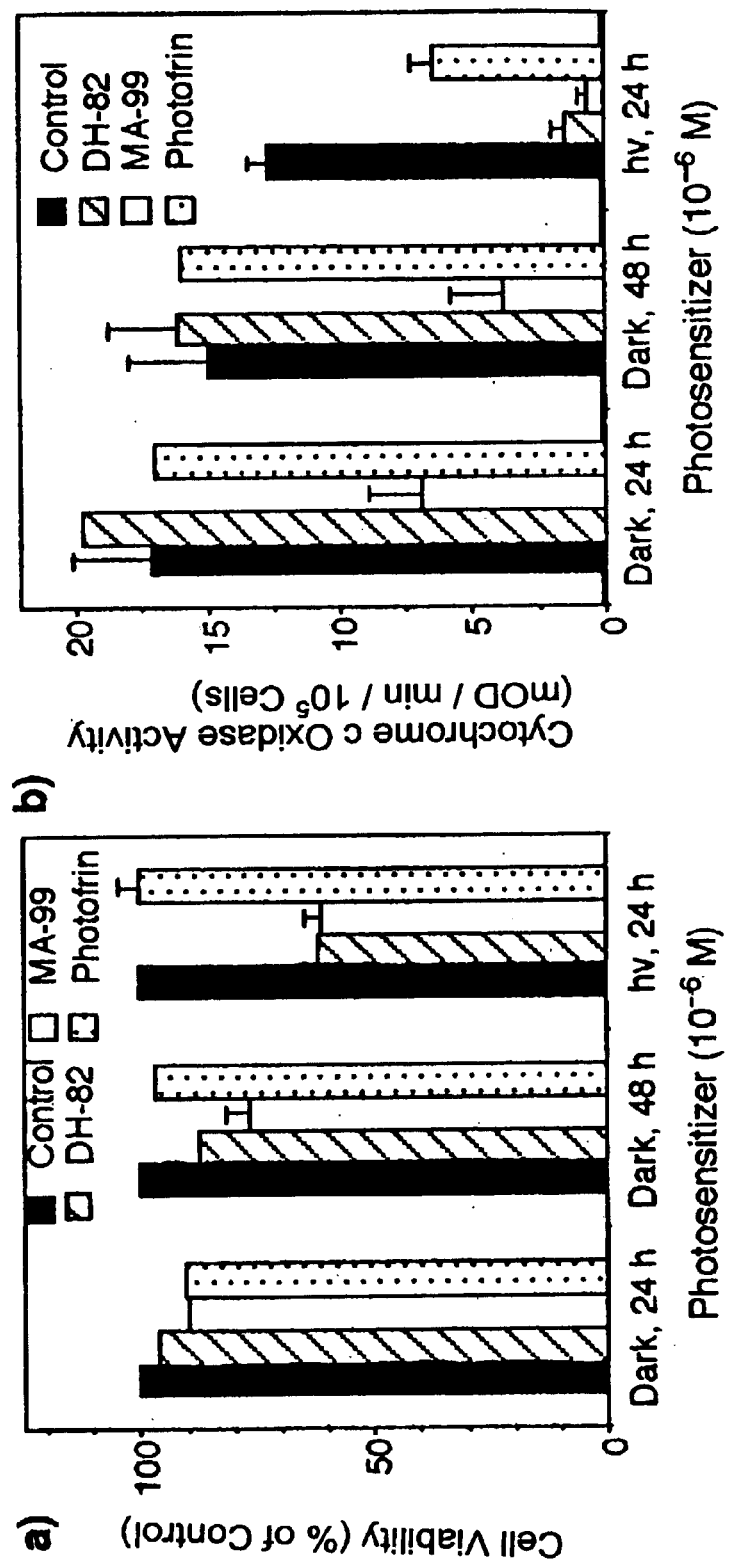
FIGS. 8a and 8b are graphical representations of the effects of certain compounds on the viability of R3230AC rat mammary adenocarcinoma cells in culture.

One observation with the photosensitizers of FIG. 14 concludes that carboxylate salts impart much greater phototoxicity than the corresponding sulfonate salts based on the significantly lower values of $EC_{50}$ (Table 1). The mitochondria have been identified as an important cellular target for porphyrin-related molecules and we compared the sulfonate salt DH-82 and the carboxylate salt MA-99 with Photofrin® for their effects on cellular cytochrome c oxidase activity. The data in FIG. 8a show the effects of the addition of $10^{-6}$ M DH-82, MA-99, or Photofrin® on the viability of R3230AC cells in culture in the dark for 24 or 48 h or 24 h after exposure to 0.9 J cm$^{-2}$ of 590–750 nm light delivered at 0.5 mW cm$^{-2}$. At this concentration, the photosensitizers were minimally toxic with DH-82 and MA-99 inducing a 20–30% reduction in cell number in the dark after a 48-h exposure and a 40% reduction in cell number 24 h after light exposure.

In parallel experiments, mitochondrial cytochrome c oxidase activity was determined after exposure of R3230AC cells to the same porphyrins either in the dark or 24 h after light exposure (FIG. 8b). DH-82 and Photofrin® are comparable to controls with respect to inhibition of cytochrome c oxidase in the dark showing little if any inhibition. In contrast, MA-99 inhibited whole cell cytochrome c oxidase activity by 60% after a 24-h incubation period in R3230AC cells. Twenty-four hours after irradiation with 0.9 J cm$^{-2}$ of 590–750 nm light, enzyme activity in cells incubated with Photofrin® was reduced by 50% compared to control untreated cells and by 90% in cells treated with DH-82. Cytochrome c oxidase activity in R3230AC cells irradiated in the presence of MA-99 was inhibited by 95%, a 5–10% further reduction in enzyme activity compared to that obtained from cells incubated with MA-99, but not exposed to light. Taken together, these data indicate that DH-82, MA-99, and Photofrin® impact the function of an important mitochondrial enzyme, cytochrome c oxidase, which is involved in cellular respiration. However, the photosensitizers impact the function in different ways: MA-99 was a potent inhibitor of enzyme activity in the dark and after light exposure while DH-82 and Photofrin® were only effective after exposure to light.

In Vivo Studies with Core-Modified Porphyrins. A. Preliminary Studies of Toxicity.

With porphyrin-related photosensitizers, the therapeutic dose for rodents is typically 1–5 mg/kg. Initially, a starting dose of 10 mg/kg was used to evaluate the core-modified porphyrins for dark toxicity. In groups of five BALB/c mice given a single intravenous injection of 10 mg (10 $\mu$mol)/kg of dithiaporphyrin DH-82, 10 mg (10 $\mu$mol)/kg of diselenaporphyrin DH-105, or 10 mg (12 $\mu$mol)/kg of dithiaporphyrin MA-99 as a saline solution, neither toxicity nor morbidity was observed. The animals were followed for 90 days post-injection under normal vivarium conditions (daily cycle of 12 h of fluorescent light/12 h of darkness). After sacrifice, no gross abnormalities were noted in the organs and tissues of sacrificed animals. As described below, this treatment dose with DH-82 was 0.13 mg (0.13 $\mu$mol)/kg and with MA-99, 0.15 mg (0.19 $\mu$mol)/kg, which corresponds to a therapeutic index of >65 for each of these compounds.

For comparison purposes and for a more thorough study of structure/activity relationship in core-modified porphyrins, core-modified porphyrins containing the heavier chalcogen atom selenium are used. It should be noted that in these molecules, the selenium atom is an added concern for clinical applications as a potential source of toxicity. However, selenium is an essential trace element and has been the subject of numerous toxicity studies. No toxicity from selenium has been observed in subjects receiving up to 724 $\mu$g (9.20 $\mu$mol)/day over a 2-year period. Futhermore, organoselenides, such as-a selenium-containing core-modified porphyrin, exhibit less toxicity on an equivalent basis than either the free metal or inorganic selenium salts. The diselenaporphyrin DH-105 showed no abnormal toxicity as described above and has efficacy comparable to that of Photofrin® upon irradiation. A major advantage of DH-105 relative to Photofrin® is greatly reduced skin photosensitization as described below.

Preliminary Distribution Studies with Core-Modified Porphyrins.

Figure 9:
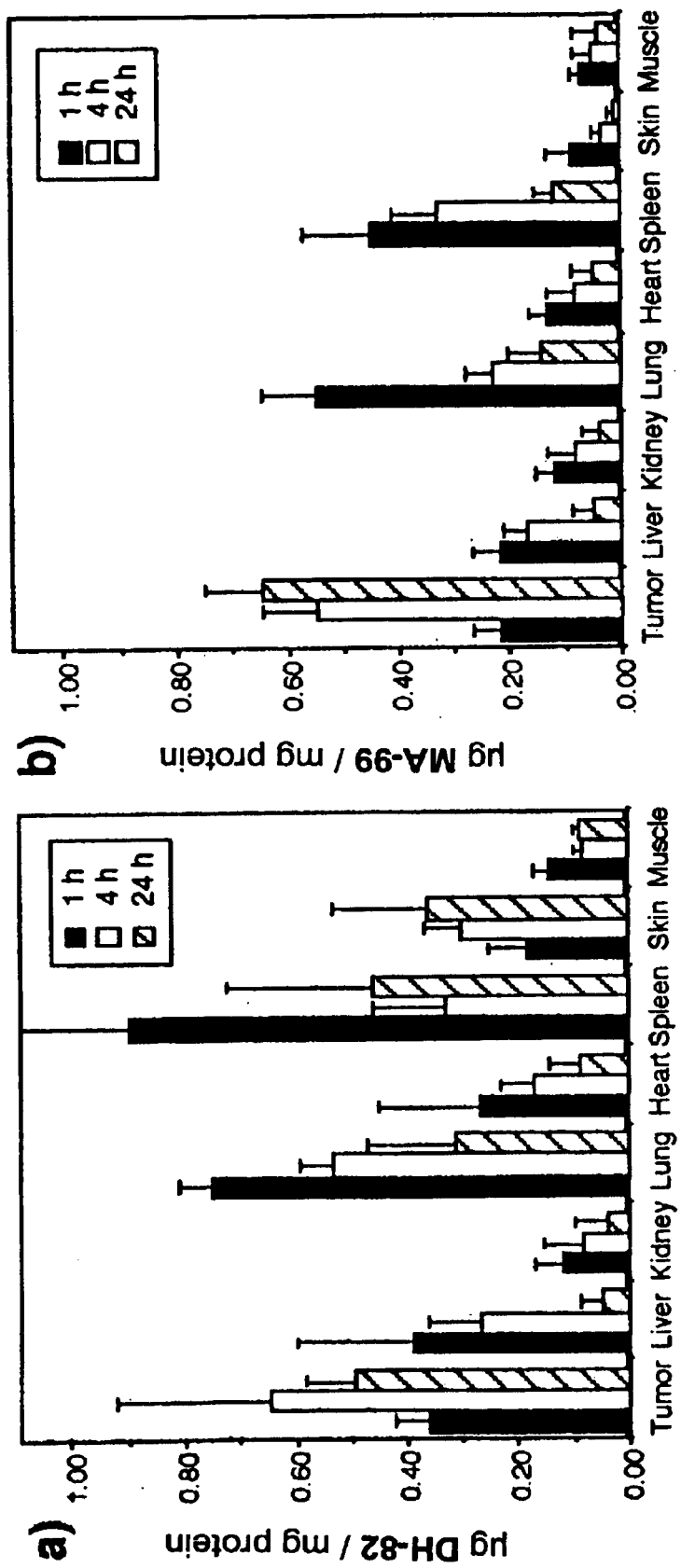
FIGS. 9a and 9b are graphical representations of the tissue distribution of certain compounds in various organs of BALB/c mice bearing Colo-26 tumors.

The fluorescence associated with DH-82 and MA-99 facilitated distribution studies with these two sensitizers (Table 2). In BALB/c mice bearing Colo-26 tumors, the presence of photosensitizer was measured by fluorescence spectroscopy of digested tissue at 1, 4, and 24 h post-injection of 5 mg (5 $\mu$mol)/kg of DH-82 or 2.5 mg (3.2

μmol)/kg of MA-99 (FIG. 9). For both DH-82 and MA-99, the highest concentration of photosensitizer was observed at 1 h post-injection in the liver, kidney, lung, heart, spleen, and muscle with decreasing concentrations at 4 and 24 h post-injection. In the tumor, concentrations of photosensitizer increased between 1 h and 4 h post-injection and comparable concentrations of DH-82 or MA-99 were found between 4 and 24 h post-injection. Furthermore, at 24 h post-injection, the concentration of DH-82 or MA-99 is higher in the tumor than in the other tissues examined. The most striking difference in the distribution of the two sensitizers was found in the skin. For DH-82, the concentration in skin increased from (0.18±0.07) μg/mg of protein at 1 h post-injection to (0.36×0.13) μg/mg of protein at 24 h post-injection. In contrast for MA-99, the concentration in skin decreased from (0.09±0.04) μg/mg of protein at 1 h post-injection to (0.01±0.01) μg/mg of protein at 24 h post-injection. The decreased concentration in the skin may partially explain the lack of skin photosensitization observed with MA-99.

The derivatives of core-modified porphyrins that have been examined have greatly increased the uptake of photosensitizer in tumor from compound 6. A concentration of (0.019±0.007) μg of 6/g of protein was measured 24 h post-injection of 5 mg (5 μmole)/kg of 6 into BALB/c mice bearing Colo-26 tumors[58]. In contrast, a concentration of (0.49±0.09) μg of DH-82/g of protein was measured in the tumors of animals 24 h post-injection of 5 mg (5 μmole) of DH-82/kg (FIG. 9) and a concentration of (0.65±0.10) μg of MA-99/mg of protein was measured in tumors 24 h post-injection of 2.5 mg (3.2 μmol) of MA-99/kg. The structural changes from compound 6 to DH-82 and MA-99 lead to a greater than twenty-fold increase in photosensitizer uptake in tumor.

Clearance Studies Using Ear-Swelling Response as an End Point.

Figure 10:
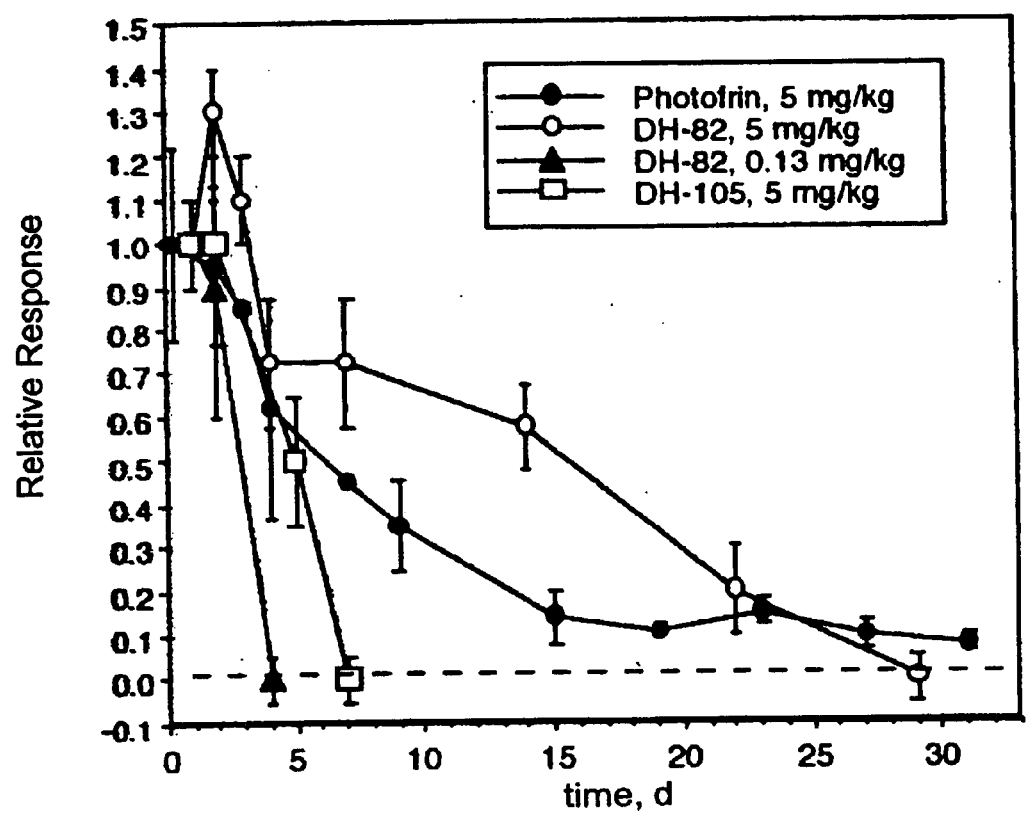
FIG. 10 is a graphical representation of the clearance time of certain sensitizers from BALB/c mice.

With Photofrin® and related porphyrin photosensitizers, long-term acute cutaneous photosensitivity remains a significant side effect in their clinical use. The issue-of long-term skin photosensitization in core-modified porphyrins has not been previously addressed and therefore examined the clearance of DH-82, DH-105, and MA-99 relative to Photofrin®. The time course of acute cutaneous photosensitivity following administration of DH-82, DH-105, or MA-99 was examined using the established murine ear swelling response (ESR) as an end point. Results obtained with a therapeutic dose (as described below) are shown in FIG. 10. The data for DH-82, DH-105, and MA-99 were compared to the ESR observed in Photofrin®-treated (5 mg/kg) mice as illustrated in FIG. 10. The absolute ESR at day 1 for DH-82 at either 5 mg/kg or 0.13 mg/kg or for DH-105 at 5.0 mg/kg was on the order of 0.11–0.13 mm swelling above the normal untreated ear thickness of 0.25–0.30 mm. The absolute swelling observed with Photofrin®-treated animals on day 1 was larger —on the order of 0.20–0.25 mm. To facilitate comparisons, the ear-swelling responses for Photofrin®, DH-82, and DH-105 at day 1 were each assigned a relative value of 1.00. The ESR disappeared between 22 and 29 days in animals treated with DH-82 at 5 mg/kg. Replacing the two sulfur atoms of DH-82 with selenium atoms in DH-105 eliminated the ESR between 5 and 7 days with 5 mg/kg of DH-105 (FIG. 10). Lowering the dose of DH-82 to 0.13 mg/kg (the treatment dose for the PDT studies described below) eliminated the ESR between day 2 and day 4. MA-99 at 0.15 mg/kg showed no ear swelling response —either immediately after injection or at day one and beyond. Ear thickness immediately prior to treatment, immediately after treatment, and at day 1 was identical (four animals per point). In contrast, Photofrin®-treated animals show a positive ESR at 31 days post-injection. At higher light doses, the ESR is stronger in Photofrin®-treated animals. Hence, at lower treatment doses of DH-82, long-term acute skin photosensitization appears to be much less than the level seen with Photofrin®. Replacing the sulfonato groups in DH-82 with the carboxylatomethoxy substituents of MA-99 completely eliminated the ESR while maintaining efficacy, which means the structure/activity relationship studies demonstrate that these compounds minimize skin photosensitization. Furthermore, the early clearance of DH-105 relative to DH-82 when administered at 5 mg/kg disclose that heteroatom substitution minimizes long-term skin photosensitization.

There were no ill effects from the combination of drug and light in 15 animals receiving 5 mg/kg of DH-82, in 15 animals receiving 5 mg/kg of DH-105, or in 12 animals receiving 0.15 mg/kg of MA-99 and irradiated on their ears with 135 J cm$^{-2}$ of 694-nm light at various time points. Although there was some transient swelling in the ears with DH-82 and DH-105, there was no necrosis.

PDT with 21,23-Core-Modified Porphyrins.

Isoeffective doses for the various 21,23-core-modified porphyrins were determined from the values of $EC_{50}$ in Table 1 assuming that the cell model in vitro translates to performance in vivo. As a starting point, approximate isoeffective doses were based on the published conditions for PDT with Photofrin® at 2.5 mg (4.0 μmol)/kg. Diselenaporphyrin DH-105 ($EC_{50}$ of 7.9 μM) and Photofrin® ($EC_{50}$ of 9.0 μM) should have comparable isoeffective doses. In contrast, both dithiaporphyrin DH-82 ($EC_{50}$ of 1.6 μM) and MA-99 ($EC_{50}$ of 0.43 μM) should have significantly smaller isoeffective doses than either DH-105 or Photofrin®.

Groups of BALB/c mice bearing Colo-26 tumors were given 2.5 mg (2.5 μmol)/kg of diselenaporphyrin DH-105, 0.13 mg (0.13 μmol)/kg of dithiaporphyrin DH-82, or 0.15 mg (0.19 μM)/kg of dithiaporphyrin MA-99 —all as a 5% dextrose in water solution via tail-vein injection. The animals were irradiated 4 h post-injection with 135 J cm$^{-2}$ of 694-nm red light from a dye laser (75 mW cm$^{-2}$ for 30 min). The time in days to 400-mm$^3$ tumor volume was noted for each animal in each group and the results are presented as a Kaplan-Meyer plot in FIG. 11. For comparison purposes, BALB/C mice bearing Colo-26 tumors were given 2.5 mg (4.0 μmol)/kg of Photofrin® as a 5% aqueous dextrose solution and were irradiated 24 h later with 135 J cm$^{-2}$ of 630-nm laser light at a power of 75 mW cm$^{-2}$ for PDT with Photofrin®.

Figure 11:
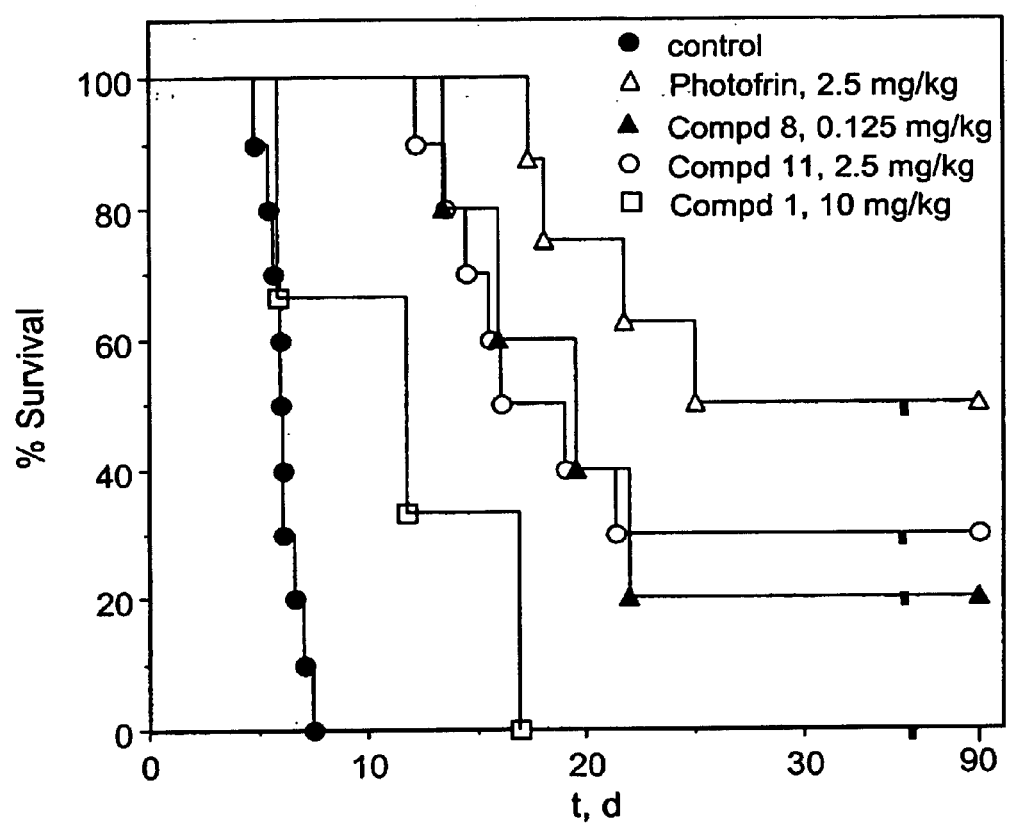
FIG. 11 is a Kaplan-Meyer plot for PDT with certain compounds against implanted Colo-26 tumors in BALB/c mice.

Of the eight animals treated with Photofrin, ® four cures were obtained (no tumor regrowth detected 90 days post-treatment) and the other four animals gave a mean time to 400 mm$^3$ of 21±4 d as shown in FIG. 11. DH-105 and Photofrin® have nearly identical values of $EC_{50}$ and animals received identical 2.5 mg/kg doses of photosensitizer DH-105. In ten animals treated with diselenaporphyrin DH-105 and light, three cures were obtained and the other seven animals gave a mean time to 400 mm$^3$ of 17±3 d. These results are statistically different than results from untreated controls (P <0.001), but are not significantly different than PDT with Photofrin® (P >0.59, FIG. 11).

Both DH-82 and MA-99 have $EC_{50}$ values (Table 1) much lower than that of Photofrin®. Consequently, much smaller doses of these two photosensitizers were used. Of the five animals treated with dithiaporphyrin DH-82 [0.13 mg (0.13 μmol)/kg] and light, one cure was obtained and the other four animals gave a mean time to 400 mm$^3$ of 18±4d, which represented a 300% increase relative to untreated controls (6±2 d, P <0.001), but not significantly different than PDT with Photofrin® (P >0.59, FIG. 11). The treatment dose with DH-82 is roughly 5% of the treatment dose with Photofrin® by weight and roughly 3%, by molar amounts. Based on values of $EC_{50}$, one would expect PDT with MA-99 to be more effective than PDT with DH-82 at a comparable dose. Of the eight animals in our initial study with MA-99 at 0.15 mg (0.19 μmol)/kg, five cures were obtained and the other three animals gave a mean time to 400 $mm^3$ of 23±7 d, which is not significantly different from PDT with Photofrin® (P >0.59). The efficacy using DH-82 and MA-99 as photosensitizers is clearly comparable to that of Photofrin® at much higher concentrations.

Summary of Data.

The core-modified porphyrins are an outstanding new class of photosensitizers for PDT. Their physical and photophysical properties are well suited to be effective photosensitizers. More importantly, structure/activity relationship studies demonstrate that efficacy and skin photosensitization are manipulated through proper substituent choices. For photophysical properties, the band I absorption of 5,10,15, 20-tetraaryl-21,23-core-modified porphyrins is stronger and at longer wavelengths than the band I absorption of the corresponding tetraaryl porphyrins. In addition, the 21,23-dithiaporphyrins are fluorescent following excitation by either one- or two-photon processes, which permits fluorescent imaging techniques to follow the time-course of distribution as well as cellular sites of localization and to quantify uptake of sensitizer in various tissues. The core-modified porphyrins generate singlet oxygen efficiently upon irradiation of band I with quantum yields [$\phi(^1O_2)$] typically $\geq 0.50$. Furthermore, the core-modified porphyrins are less prone to photobleaching than Photofrin®, which is a consequence of their non-planarity (due to the larger core heteroatoms).

These phototoxicity results of core-modified porphyrins toward Colo-26 cells in vitro disclose that two water-solubilizing groups at adjacent meso-positions and two hydrogen-bond-accepting substituents at the other two meso-substituents provide more potent photosensitizers in the series. Furthermore, the water-solubilizing group also impacts the effective concentrations for PDT in vitro and impacts the initial site of cellular localization. Studies of cytochrome c oxidase activity in whole cells disclose that the mitochondria are an important target for PDT with the core-modified porphyrins. Relative phototoxicities of the core-modified porphyrins in vitro-are used to approximate isoeffective doses for PDT in vivo.

The issue of long-term skin photosensitization is addressed through structure/activity relationship studies, as well. At equal doses of 5 mg/kg, diselenaporphyrin DH-105 gives much less skin photosensitization than dithiaporphyrin DH-82. Replacing the sulfonato solubilizing groups of DH-82 with the carboylatomethoxy groups of MA-99 gives a photosensitizer with no detectable ear swelling response. Choices in the meso-substituents and the 21,23-heteroatoms impact skin photosensitization while maintaining efficacy.

As shown in FIG. 14, we have already prepared derivatives of DH-82 with different chalcogen atom substitutions (10–12 and DH-105) and different meso-aryl substituents (13–15 and MA-99). We have prepared other derivatives selected for different solubilizing groups in the 5,10-positions (arylcarboxylate salts, free phenols and PEGylated phenols), optimal substituted aryl groups in the 15,20-positions, and combinations of heteroatoms (S/Se and Se/S in addition to S/S and Se/Se) in the 21,23-positions. The proper balance of electronic factors, lipophilicity/hydrophobicity, hydrogen-bond donors or acceptors, and substituent pKa's provide general insight for the design of photosensitizers as well as clinically viable core-modified porphyrin photosensitizers.

Two novel properties for the proposed materials of this invention include 1) replacing two nitrogen atoms in two pyrrole rings of 5,10,15,20-tetra(aryl)porphyrins with two chalcogen atoms (sulfur and/or selenium) and 2) having two solubilizing aryl groups at the 5- and 10-positions of core-modified porphyrins. The substitution of chalcogen atoms for nitrogen atoms leads to absorbance of longer wavelengths of light ($\geq 690$ nm) allowing greater penetration of light into tissue, high quantum yields for the generation of singlet oxygen, rapid cellular uptake of sensitizer both in vitro and in vivo, and efficacy both in vitro and in vivo. In addition, DH-82 at a therapeutic dose of 0.13 mg/kg exhibits no acute cutaneous skin photosensitization between 2 and 4 days post-injection and that MA-99 at a therapeutic dose of 0.15 mg/kg exhibits no skin photosensitization in a murine model.

In the preparation of selenium-containing materials, precautions are taken to avoid the ingestion of selenium-containing compounds.

In Vitro Studies. Initial phototoxicity assays use human squamous carcinoma cells (FaDu), murine colon carcinoma cells (Colon-26), rat mammary adenocarcinoma cells (R3230AC), and non-malignant monkey kidney epithelial (CV-1) cells. Lack of phototoxicity on CV-1 cells correlates with sparing of early passage keratinocytes. Colony forming assays in multi-well plates typically use irradiation at 600–800 nm with a total fluence of 24 J $cm^{-2}$ and 6 dye concentrations (0.1 to 50 μM), although light dose and concentrations are adjusted as necessary. Laser sources with a diffusion tip will be used where appropriate (20 J $cm^{-2}$ fluence). Sensitizer potency will be characterized by the concentration giving 50% survival ($LC_{50}$). Controls for cells irradiated in the presence of selected sensitizers will be cells that receive no treatment, cells exposed to sensitizer alone without irradiation (dark controls) and cells exposed to light in the absence of sensitizer (light controls). Sensitizers will be ranked on the basis of their $LC_{50}$ and the most promising, those that provide the greatest phototoxicity (comparable to or greater than DH-82) with the least dark toxicity, will be selected for further study. Dark toxicity and phototoxicity will be compared statistically using the SAS statistical program (SAS, Inc., Cary, N.C.). A P-value of <0.05 is considered significant.

Cells maintenance will be performed using 100-mm culture dishes with 10 mL of minimum essential media supplemented with 10% fetal bovine serum (FBS, Atlanta Biologicals, Atlanta, Ga.), 50 units/mL of penicillin G, 50 mg/mL of streptomycin, and 1.0 mg/mL of fungizone (MEM). When cell monolayers reach 80–90% confluency, the media is removed, 1.0 mL of 0.25% trypsin will be added, and dishes incubated for 3–5 min at 37° C. until cells detach from the surface. The appropriate number of cells (2 to 4X $10^6$) are transferred to new 100-mm dishes containing 10 mL MEM. Only cells from passage 10 or lower are used for experiments. Stocks of cells from passages 1–4 will be stored at −86° C. and used to initiate cultures.

Photosensitizer uptake experiments are conducted with fluorescent sensitizers. First, cells will be removed from 100-mm dishes by trypsinization (see above) and seeded on 96-well plates at $5 \times 10^4$ cells/well in 200 μL of MEM. Twenty-four hours after cell seeding, the media is removed and 200 µL of MEM containing sensitizer at $1\times10^{-6}$ to $1\times10^{-3}$ M is added. To establish baseline fluorescence, control cells incubated with MEM not containing any photosensitizer are used. At 1, 3, 6, or 24 h after sensitizer addition, the sensitizer-containing media is removed from wells selected for each time point. The monolayers are washed once with 200 µL of 0.9% NaCl and 200 µL of MEM minus FBS and phenol red is added. Fluorescence of the cells is determined using a Spectramax Gemini spectrofluorimeter (Molecular Devices, Sunnyvale, Calif.). Sensitizers will be compared according to the rate at which the fluorescence approached its maximum final emission per $10^5$ cells as well as by the final sensitizer concentrations in cells. The fluorescence values calculated for $10^5$ cells will be compared to a standard curve of fluorescence obtained from known concentrations of each sensitizer.

Mechanisms and Sites of Photodamage.

Photochemical mechanisms are examined in greater detail by determination of sites of intracellular localization and mechanisms of phototoxicity for each photosensitizer. Epifluorescence microscopy is used where possible to determine sensitizer localization. In this technique, monolayers of cells incubated with sensitizer are washed and examined under a Zeiss Axovert microscope. Epifluorescence is excited with low intensity light from either a filtered xenon source or an argon pumped dye laser tuned to an appropriate absorption of the sensitizer. The cells are viewed using a double microchannel plate intensifier and CCD video camera coupled to a computer-based imaging system. As an example, fluorescence from the sensitizer is granular if mitochondria are targeted. Alternatively, two-photon excitation of the photosensitizers is used with the confocal microscope to follow cellular distribution of the photosensitizer.

Studies of whole cell respiration and dark and light induced changes to mitochondrial function in isolated mitochondria were performed to determine sites of photodamage for each sensitizer. The effects of irradiation at multiple sites in the oxidation and phosphorylation pathways suggest sites of attack as well as the importance of oxygen in the phototoxic response. The importance of singlet oxygen were evaluated by the effects of added singlet-oxygen quenchers and by the effects of reduced partial pressures of oxygen surrounding drug-treated mitochondrial suspensions. If oxygen dependence was not confirmed, other mechanisms involving photo-induced electron transfer or photoisomerization of the sensitizer were responsible for the phototoxic response.

Photosensitization of Mitochondrial Cytochrome c Oxidase.

In vitro studies of the effects of sensitizers on mitochondrial function, using cytochrome c oxidase as a representative marker, is performed using mitochondrial suspensions prepared from R3230AC rat mammary adenocarcinomas. Sensitizers are prepared by dissolving 2.0 to 2.5 mg of sensitizer in 2.5 mL of 95% ethanol and adjusting the concentration of the sensitizer so that 10 µL/mL of mitochondrial preparation buffer has an absorbance between 600 and 800 nm of between 0.2 and 0.25 absorbance units (A.U.). Mitochondria are thawed at room temperature and the activity of the cytochrome c oxidase adjusted to yield a change of 0.45 to 0.6 A.U. per minute at 550 nm when 10 µL of mitochondria are added to the cytochrome c reaction mixture. Ten microliters of sensitizer solution is then added to 1.0 mL of mitochondrial suspension, mixed with a Pasteur pipette and incubated for 5 min at room temperature in the dark. The sensitizer/mitochondria mixture is then centrifuged in an Eppendorf microfuge for 5 min, the supernatant is removed, and the mitochondria are resuspended in 1.0 mL of mitochondrial preparation buffer. The mitochondrial suspension is then transferred to a 3.0 mL quartz cuvette that had been previously positioned in the 1.0-cm diameter beam of a focused and filtered (530 to 800 nm) 1000 W tungsten light source. Suspensions are stirred magnetically while irradiation is carried out at 100 mW/cm$^2$. At selected times, from 0 to 60 min, 10 µL aliquots are removed for measurement of cytochrome c oxidase activity. A separate suspension remains in the dark and comparable samples are removed to serve as controls. Three to five separate experiments will be performed for each sensitizer and the data calculated as the percent of initial enzyme activity.

Determination of the effects of dyes on intracellular mitochondrial cytochrome c oxidase are performed on cultured R3230AC cells. Cultures are seeded at $1\times10^5$ cells/well on 12-well plates in 1.0 mL MEM (described above). Twenty-four h later, sensitizers are added at concentrations ranging from $10^{-4}$ to $10^{-6}$ M. Cells are incubated in the dark with the sensitizers in MEM for 24 h in a 37° C. incubator. The sensitizer containing medium are then removed and 1.0 mL of MEM minus phenol and FBS added to each well. Selected plates are then irradiated at 0.5 mW cm$^{-2}$ for 0.5 to 1 h using a filtered (590–750 nm) tungsten source. The medium is removed and 1.0 mL/MEM plus phenol and FBS added. Cells are incubated as above for 24 h, medium removed, and cells detached using trypsin. Cell suspensions, 3 wells/sample, are then centrifuged and resuspended in 100 µL MEM minus phenol and FBS and stored frozen at −70° C. until used for cytochrome c oxidase determinations. Cell counts on single wells are made 24 h after dye addition (24-h dark control), 24 h later on plates maintained in the dark (48-h dark controls), and on plates exposed to light (24-h light samples). Cytochrome c oxidase is measured as above after cell suspensions are thawed and sonicated on ice after 30 s at 10 s bursts using a Branson probe sonifier set at a power of 2. The whole-cell lysate is added to the cytochrome c reaction mixture and results are expressed as the amount of cytochrome c oxidase activity per $10^5$ cells. From these experiments, the most potent sensitizers (i.e., those sensitizers that are comparable to or better than DH-82 and MA-99) are selected for further in vitro and in vivo experiments.

Effects of Oxygen Radical Quenchers on Photosensitized Inhibition of Cytochrome c Oxidase.

The experiments described above will first be performed in the absence of oxygen in a chamber designed to be evacuated and then filled with nitrogen. Oxygen in the chamber and the mitochondrial suspension are maintained at 0±0.4% throughout the irradiation period by replacement with nitrogen. Those sensitizer candidates whose potency is inhibited in the absence of oxygen are tested further to determine the involvement of singlet oxygen or superoxide while those that retain their potency are altered chemically to determine the mechanism of action. Either 8 or 80 mM imidazole or 1 or 10 µg/mL superoxide dismutase is added to the mitochondrial suspensions prior to irradiation and measurements of cytochrome c oxidase activity, i.e., inhibition is measured in the presence or absence of these quenchers.

In Vivo-In Vitro Photosensitization of Mitochondrial Cytochrome c Oxidase.

Tests are performed to take into account what impact the metabolism of the host might have on the photosensitizing potency of the sensitizers selected from the above experiments. Experiments were performed as described above, except that the mitochondria is obtained from R3230AC tumors borne on animals injected i.v. (tail vein) with 5 mg/kg of each sensitizer selected (or less if 5 mg/kg is toxic). A starting point for both DH-82 and MA-99 was 0.25 mg/kg. The period between the time of sensitizer administration and excision of tumors and preparation of mitochondria was determined-by time-course and distribution studies described below. The ideal time period was defined as the time 3 to 48 h post-injection either where sensitizer is at its highest concentration in tumor or where the ratio of sensitizer in tumor to sensitizer in normal tissues (liver, lung, kidney, heart) is highest.

Lysosomal Selectivity.

Lysosomal selectivity of the core-modified porphyrin sensitizers were evaluated using two methods. First, localization studies were performed using very low light fluorescence microscopy of cells in vitro exposed to the chalcogen-containing sensitizer. Second, inhibition of lysosomal-specific hexosaminidase by photosensitization of cells in culture exposed to the chalcogen-containing sensitizers were performed. Hexosaminidase activity was determined according to conventional methods. The results from those studies allowed us to assess the specificity of these classes of photosensitizing agents for lysosomes.

Photosensitizer Induced Apoptosis.

For the dyes that have the most desirable characteristics, we examined their mode of phototoxicity by determining the level of necrosis or apoptosis induced in cell culture. Cells were exposed to selected sensitizer concentrations and light fluences to induce a cytotoxicity of 50% as determined earlier using the colony-forming assay for cell viability. Apoptosis and/or necrosis was detected in sensitizer/light exposed cells using the ApopNexin™ detection kit (Oncor, Gaithersberg, Md.). The kit contains Annexin V conjugated with fluoroscein isocyanate (FITC), a reagent that binds specifically to phosphatidyl serine, which becomes exposed on the plasma membrane early during apoptosis. Also included is propidium iodide, which labels necrotic cells. Following incubation with the ApopNexin™ reagents, cells were sorted via flow cytometry and the complement of necrotic vs. apoptotic cells were determined.

In Vivo Studies- Short-Term Toxicity.

The initial evaluation determined the degree of dark toxicity (approximate $LD_{10}$) in BALB/c mice and, for promising candidates, in Fischer 344 female rats as a second model. Groups of 5 animals will be given a single, intravenous injection of sensitizer and observed for 48 h for toxicity and morbidity. Larger groups (10–20 animals) were given a single intravenous injection and observed for 30 days to define the $LD_{10}$. The starting sensitizer dose for subsequent in vivo efficacy and pharmacokinetic studies were defined as 5 µmol/kg or 90% of the $LD_{10}$, whichever is smaller. Some candidates were eliminated at this point because of toxicity.

Candidates with acceptable dark toxicity were examined for toxicity in BALB/c mice receiving sensitizer and light. Starting with 5 µmol/kg or 90% of the $LD_{10}$, whichever is smaller, animals were given decreasing dosages of sensitizer (one possible series: 5 µmol/kg, 1.5 µmol/kg, 0.5 µmol/kg, and 0.05 µmol/kg) followed by irradiation of depilated abdomen or shoulder at various time points (i.e., 3, 6, 12, and 24 h post-injection) with a constant light dose (135 J $cm^{-2}$ from a laser of appropriate wavelength is a typical example) to examine acute phototoxicity, as measured by the development of erythema.

Tumor Models.

The subcutaneously transplanted Colon-26, RIF (radiation induced fibro-sarcoma), and SMT-F (spontaneous mammary carcinoma, fast growing) tumors were used as murine models in vivo. The Colon-26 line is particularly useful because it grows in non-pigmented BALB/c mice and because it has a moderate level of multi-drug resistance (MDR). In some studies, human squamous carcinoma (FaDu) or colon carcinoma (CX-1) lines will be grown as subcutaneous xenograft tumors in nude mice.

As a second animal model, the subcutaneously transplanted R3230AC (rat mammary adenocarcinoma) tumors in Fischer 344 female rats were used. The R3230AC tumor is a well-differentiated adenocarcinoma that is genetically specific for the Fischer rat.

Clearance and Distribution Studies.

The kinetics of sensitizer clearance from normal BALB/c skin in Colo-26 tumor-bearing animals were determined in the initial pharmacokinetic studies. To minimize the number of sacrificed animals, an in vivo spectrophotometer was used where possible. This device can readily detect levels of sensitizer down to an injected dose of 0.1 µmol/kg for porphyrin-like molecules. Sensitizers were grouped by time to 90% clearance of maximum concentration: $\leq 1$ h, 1–6 h, 6–24 h, and >24 h.

The kinetics of dye accumulation and clearance from Colon-26 tumors and normal Balb/c skin were followed using the in vivo spectrophotometer, determining skin, (skin +tumor), and tumor levels of the photosensitizer. Using established techniques in our laboratories, at various times after sensitizer administration, transmittance of skin and tumor were measured non-invasively from 650 to 850 nm and the data converted to absorption and corrected for preinjection tissue optical properties to determine skin, (skin +tumor), and tumor levels of the sensitizer. Plasma clearance of various sensitizers were determined by removing blood from mice (heart puncture) at various times following sensitizer injection, spinning to separate plasma, and diluting into saline. The sensitizer content was measured by absorption and/or fluorescence and comparisons with standard curves was made to compute µg sensitizer/mL serum. At points of maximal tumor accumulation and of maximal selectivity, sensitizer levels in tissues were determined by direct extractions.

At various times after sensitizer administration, animals were sacrificed and sensitizer levels determined by direct extraction. In tumor-bearing animals (BALB/c mice or female Fischer rats), the concentration of sensitizer was determined by fluorescence spectroscopy where possible. At various time points post-injection of 5 µmol/kg of sensitizer or 90% of the $LD_{10}$ (whichever is smaller), tissues were removed, weighed, homogenized, and frozen in liquid nitrogen (3–5 animals per time point). The homogenate, after thawing, was taken up in Solvable and the emission from sensitizer was quantified in terms of ng of sensitizer/mg of protein. With non-fluorescent sensitizers, sensitizer content was quantified spectrophotometrically. Distribution ratios were expressed as the uptake or retention of sensitizer in tumor relative to various normal tissues. Intensified digital fluorescence microscopy and/or confocal microscopy on frozen sections of the tumors, which were prepared from samples specified for this purpose, enabled us to assess intratumor sensitizer distributions. Some sensitizer candidates were eliminated at this point because of lack of tumor selectivity.

Long-Term Skin Photosensitization.

The time course of acute cutaneous photosensitivity following administration of sensitizer were followed using the murine ear swelling response (ESR) as an end point. Groups of BALB/c mice were given therapeutic doses of sensitizer. Right ears were irradiated with light from an appropriate laser source (75 mW, 135 J cm$^{-2}$) at selected time points post-injection. Ear thickness were measured with an engineer's micrometer at 5 min (control for light-associated swelling) and 24 h post-irradiation (acute skin photosensitization response) and compared to the pre-irradiation thickness of the ears (typically, 0.25–0.30 mm). A negative response was defined by ear swelling at 24 h post-irradiation that is less than or equal to the swelling observed at the 5-min control. Swelling was evaluated over a 1 to 30 day time course.

Efficacy Studies.

Animals initially were given i.v. (tail vein) injections of sensitizer at various concentrations (0.05to 5.0 µmol/kg). Mice were restrained at various times thereafter without anesthesia in specially designed holders. Fischer 344 female rats were chemically restrained at various times thereafter. In both models, tumors or normal back skin were exposed to light from a xenon arc lamp with appropriate filters or to a dye laser tuned to the absorption maximum determined by in vivo reflectance measurements. Power density of delivered light typically fell in the range of 10–200 mW cm$^{-2}$ evenly distributed to a spot size of roughly 1.5 cm and measured by a radiometer. Several dose rates were explored to examine role/limitation of available oxygen on the photodynamic process. Intratumor temperatures were measured with an Omega HYP-O microthermocouple and, when necessary, a stream of nitrogen gas was used to keep intratumor temperatures below 37° C. Animals were examined and measured daily for the first 14 days post treatment and every other day thereafter until the tumors reached 400 mm$^3$ in mice or until the tumors double in size for Fischer 344 female rats or for 90 days. Tumor size were measured in two dimensions with a caliper. Time to 400 mm$^3$ or volume doubling times of tumors from control and PDT-treated groups (8–12 animals per group) were compared statistically using the SAS statistical program (SAS, Inc., Cary, N.C.). A P-value of <0.05 is considered significant. The degree of damage to the normal skin within the irradiation field also were noted. Disappearance of tumor with minimal damage to normal skin is the most desirable response. Animals are considered cured if no tumor regrowth occurs by 90 days. In all studies, three control groups were utilized in addition to the treatment group receiving both sensitizer and light: 1) a complete control receiving neither drug nor light, 2) a group receiving sensitizer only, and 3) a group receiving light only. Representative animals from each of the treatment groups were processed for histology immediately, one day, or two weeks after irradiation. Step sections through the tumor were used to define the boundaries of tumor cell damage and death as a function of distance from the skin surface.

Synthesis of Sensitizer Candidates

Figure 15:
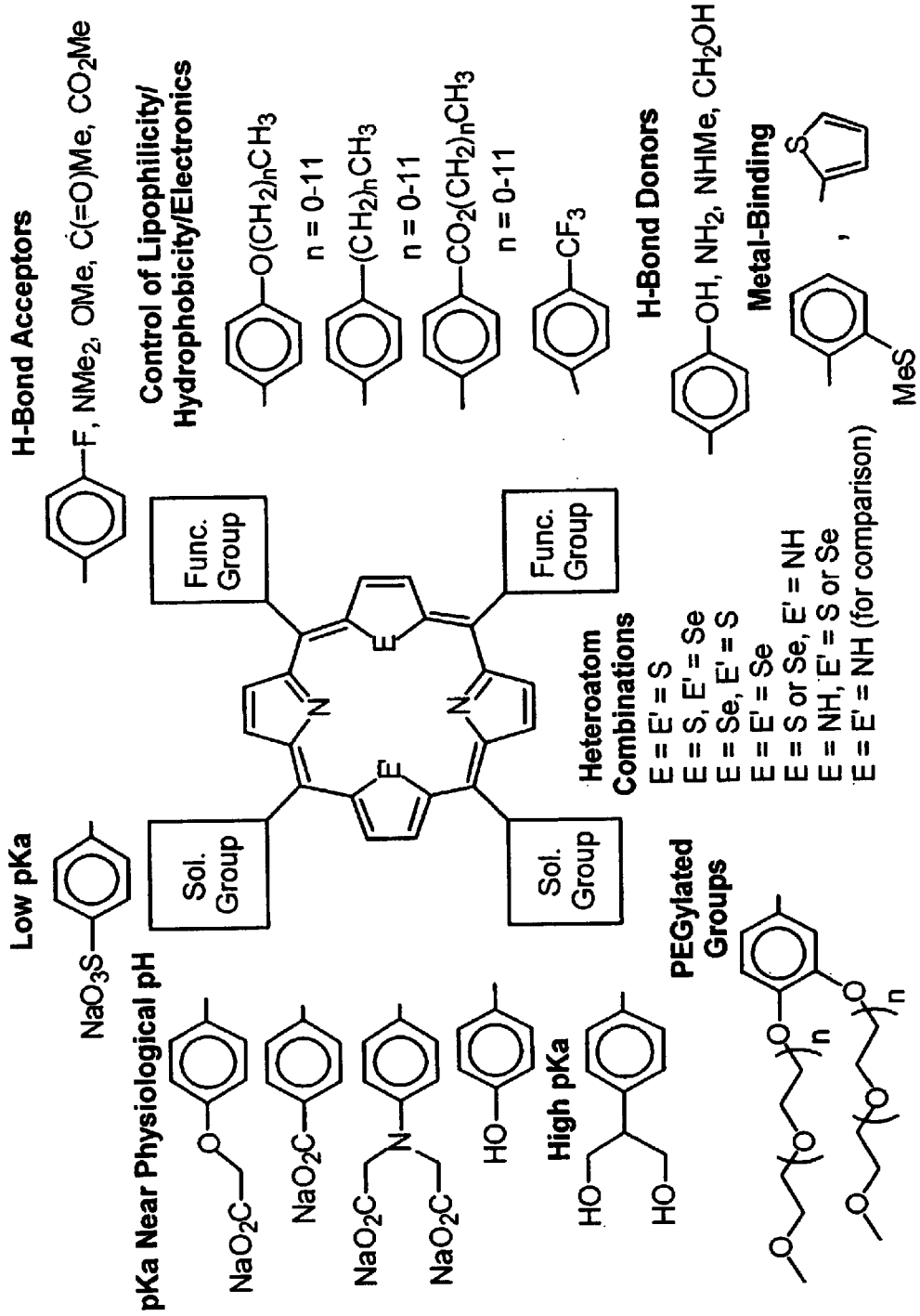
FIG. 15 illustrates a general strategy for the synthesis of compounds.

A schematic representation of our approach to derivatives for structure/activity relationship studies is shown in FIG. 15. Synthetic routes were developed to 21-thia-, 21-selena-, 21,23-dithia-, 21,23-diselena-, and 21-thia-23-selenaporphyrin photosensitizers for PDT that permit variation of substituents that impact biological properties as well as to the corresponding porphyrins for comparison purposes. Our initial work to establish structure-activity relationships (structure/activity relationship) focused on tetra(aryl)-21,23-core-modified porphyrin sensitizers that improve upon the properties exhibited by our lead compounds DH-82 and MA-99. Through our research, we have concluded that better photosensitizers have one substituent at the 5-and 10-positions and a different substituent at the 15-and 20-positions, as has been described for porphyrins and phthalocyanines; one set of substituents should be water-solubilizing groups for easy administration into patients and for ease of formulation; and hydrogen-bond accepting substituents (F, NMe$_2$) in combination with water-solubilizing groups (SO$_3$Na, OCH$_2$CO$_2$Na) provide photosensitizers with lower values of EC$_{50}$ in vitro, higher uptake in tumor in vivo, and higher efficacy at a lower dose in vivo.

For synthetic ease, we shall first address electronic factors, lipophilicity/hydrophobicity, hydrogen-bond donor/acceptor interactions, effects of metal-binding functionality, and effects from different heteroatoms in the core using various substituted aryl substituents at the meso-positions.

As an illustration of variable control, one can examine potential water-solubilizing groups. The water-solubilizing groups can be net electron-donating or electron-withdrawing substituents in their contributions to structure/activity, relationship studies, they can be strong or weak acids, or they can be non-protic as in the case of PEGylated materials (oligomeric ethylene glycol derivatives). In this application, we described our results using sulfonic acid derivatives, which have very low values of pKa relative to physiological pH. At physiological pH, the sulfonic acid derivatives are completely ionized and the sulfonate residues function as electron-withdrawing groups. The carboxylatomethoxy groups of compound 15 and MA-99 have pKa's in the 4 to 5 range (much closer to physiological pH) and are net electron-donating substituents (relative to hydrogen as a substituent) whether as the carboxylic acid or as the carboxylate salt. Benzoic acid derivatives also have pKa's in the 4 to 5 range, but the carboxylic acid form is slightly electron withdrawing relative to hydrogen while the carboxylate salt is electronically similar to hydrogen in these examples. Comparing phenylsulfonic acid and benzoic acid derivatives focus on pKa differences between two electronically similar substituents. Comparing benzoic acid derivatives with carboxylatomethoxyphenyl derivatives focus on electronic differences between groups with similar values of pKa. PEGylated aryl groups are electronically similar to carboxylatomethoxyphenyl groups. Selective choice of functionality will allow other variables to be selected similarly as hydrogen bond accepting groups that are either electron-donating or electron-withdrawing as well as groups of varying lipophilicity/hydrophobicity linked through electron-donating, electronically neutral, or electron-withdrawing functionality.

Aryl Substituents.

Figure 16:
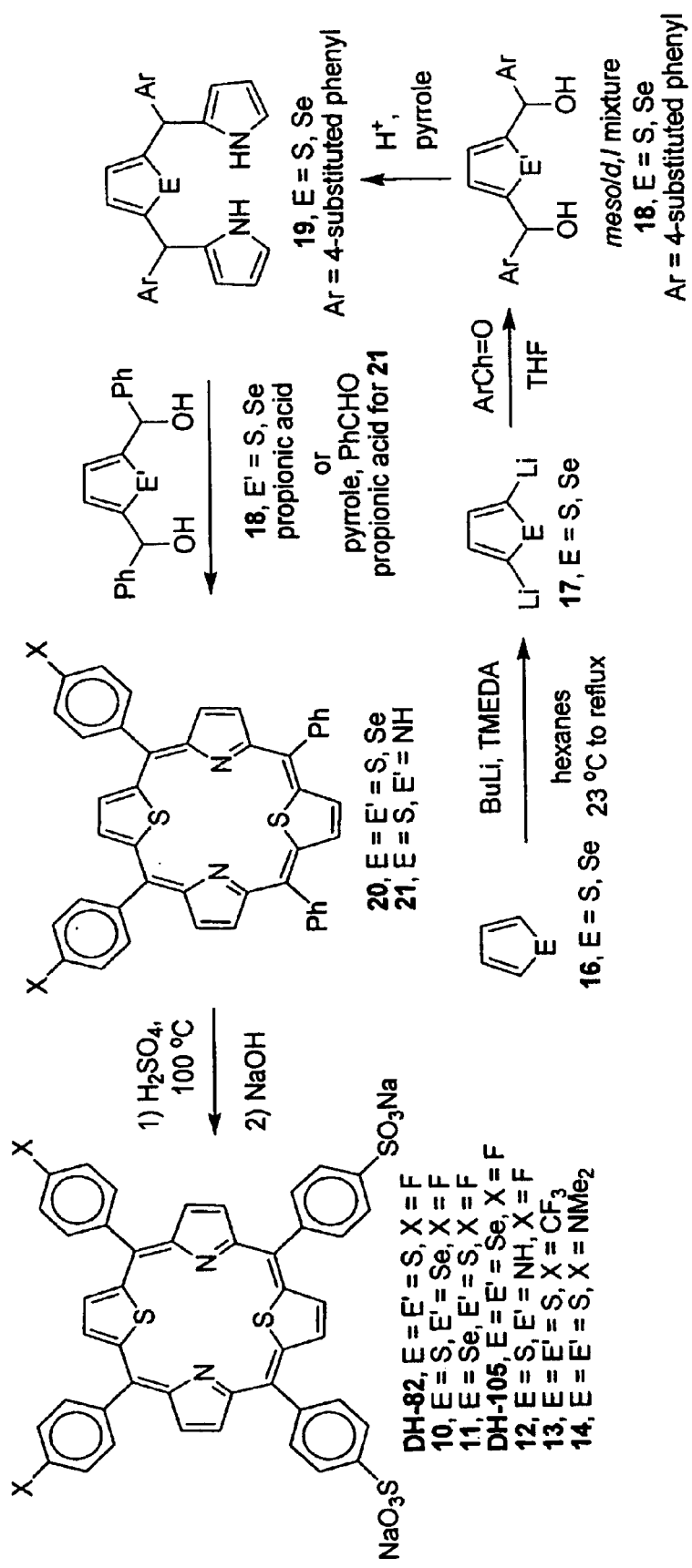
FIG. 16 illustrates the synthesis of sulfonated core-modified prophyrins.

The synthesis of a variety of different aryl substituents is shown in FIG. 16, which we have employed for the synthesis of DH-82, DH-105, and the core-modified porphyrins 10–14 listed in FIG. 14. Commercially-available thiophene (16-S) and selenophene (16-Se) are both easily dilithiated with butyllithium in hexanes to give dilithioheterocycles 17. The addition of two equivalents of an aromatic aldehyde to the dilithiochalcogenophenes 17 gives diols 18 as a mixture of meso- and d, l-diastereomers in 80–92% isolated yields. This addition has worked well with a variety of aromatic aldehydes including benzaldehyde, 4-fluorobenzaldehyde, 4-trifluoromethylbenzaldehyde, 4-methoxybenzaldehyde, 4-dimethylaminobenzaldehyde, 4-methyl-benzaldehyde (tolualdehyde), and 4-dodecylbenzaldehyde and works equally well with other 4-substituted benzaldehydes and heteroaromatic aldehydes (thiophene 2- or 3-carboxaldehyde, pyridine 2-, 3-, or 4-carboxaldehydes, as examples). The addition works equally well with 2- and 3-substituted benzaldehyde derivatives. The diols 18 are the key building blocks for the synthesis of 21,23-core-modified porphyrins.

The electrophilic addition of diols 18 to two equivalents of pyrrole is catalyzed by a strong acid (propionic acid, trifluoroacetic acid) to give the chalcogenophene bispyrroles 19 in 65 to 90% yields (FIG. 16). To prepare disulfonated derivatives, the bispyrroles 19 are condensed with a diol 18 (from the addition of benzaldehyde to 2,5-dilithiochalcogenophenes) to give 5,10-diphenyl-15,20-bisaryl-21,23-core-modified porphyrins 20. The condensation of bispyrrole 19 with pyrrole and benzaldehyde in the presence of a strong acid (propionic or trifluoroacetic) gives 21-coremodified porphyrin 21. The two phenyl rings of 20 or 21 are then sulfonated in concentrated sulfuric acid at 100° C. and treated with sodium hydroxide to generate the sodium salts in 85 to 92% yields. As stated above, this route has worked well for the synthesis of DH-82, DH-105, and core-modified porphyrins 10–14. The unsubstituted phenyl rings of 20 or 21 are preferentially sulfonated relative to the 4-substituted aryl substituents of DH-82, DH-105, and 10–14. The activating dimethylanilino substituent is protonated under the sulfonation conditions and the resulting dimethylanilinium substituent is deactivating. For the analogue of 20 with E =E'=S and X =CH$_3$, both aromatic rings are sulfonated with sulfuric acid at 100° C. to give a tetrasulfonated derivative. Similar results would be expected with other alkyl substituents. Milder reaction conditions for sulfonation allow selective sulfonation of one ring and not the other.

Activating-substituent choices may be limited in the sulfonate series if direct sulfonation is employed. However, in the series DH-82, DH-105, and 10–14 for sulfonated derivatives, core-modified porphyrins containing either electron-donating or electron-withdrawing aromatic substituents have been prepared. Two different hydrogen bond accepting substituents —the electron withdrawing fluoro substituent and the electron donating dimethylanilino substituent —have been prepared. All combinations of sulfur and selenium 21-and 23-substiuents have also been prepared.

21,23-Chalcogen Substituents.

DH-82 with two sulfur atoms in the porphyrin core has greater efficacy as a photosensitizer for PDT than DH-105 with two selenium atoms in the porphyrin core. However, DH-105 has more rapid clearance than DH-82. The change in properties with heteroatom substitution suggests that structure/activity relationship studies should incorporate various combinations of heteroatoms. Two intriguing molecules that can be prepared by the process of FIG. 16 are 21,23-core-modified porphyrins 10 and 11 that have one sulfur atom and one selenium atom in the porphyrin core. Both combinations of the two heteroatoms are easily prepared by mixing diols 18 with the opposite heteroatom in bispyrroles 19. Studies with DH-82, DH-105, 10, and 11 allow the effects of the different heteroatom combinations to be assessed in a common scaffold for physical and photophysical properties as well as properties in vitro and in vivo. A similar synthetic approach has been used to compare heteroatom effects with other aromatic substituents.

Solubilizing Aryl Groups.

While the introduction of sulfonate groups via sulfonation is a very direct and simple approach to providing water solubility in 21,23-core-modified porphyrins, uptake, distribution, and solubility are impacted by other choices of solubilizing substituents. Sulfonic acid derivatives have a very low pKa and the resulting sulfonate salts will always be ionic at physiological pH. Carboxylic acid derivatives have higher values of pKa (typically pKa's of 4 to 5), which permit both ionic and neutral forms at physiological pH. Compound 15 and MA-99 are two examples of carboxylate derivatives that we prepared.

Figure 17:
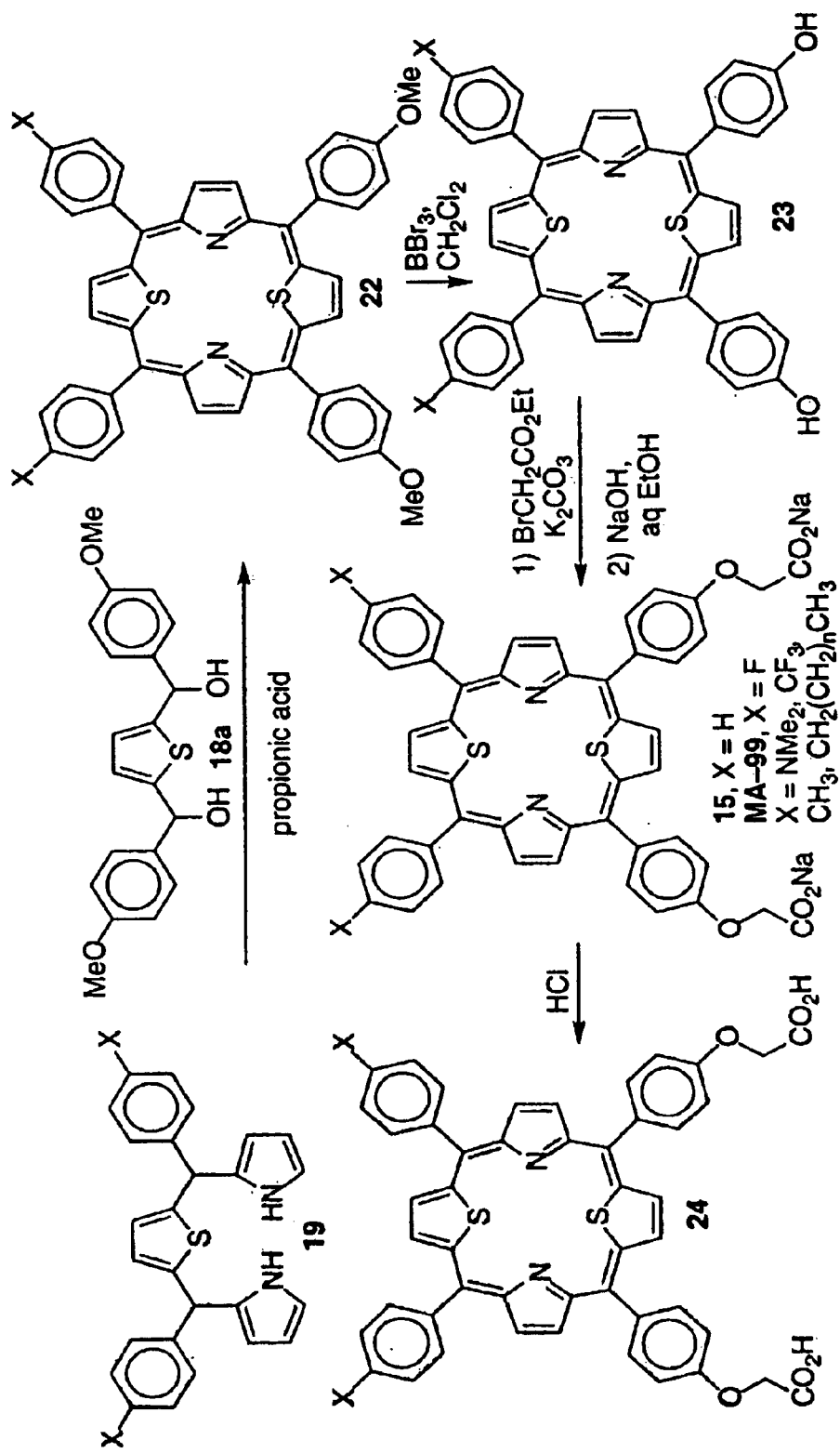
FIG. 17 illustrates the synthesis of core-modified prophyrins from bisphenol.

Compounds 15 and MA-99 were prepared as shown in FIG. 17, the acid-catalyzed condensation of bisaryl bispyrrole 19 with bis(4-methoxyphenyl) diol 18a gives the corresponding 5,10-bisaryl-15,20-bis(4-methoxyphenyl)-21, 23-ditiaporphyrin (22). Demethylation of 22 with boron tribromide in dichloromethane gives the corresponding 5,10-bisaryl-15,20-bis(4-hydroxyphenyl)-21,23-ditiaporphyrin 23. The addition of two equivalents of ethyl bromoacetate to 23 gives the bisester in 80 to 85% yields, which can be saponified with sodium hydroxide in aqueous ethanol to give the biscarboxylate salt 15 and MA-99. While the carboxylate salts provide aqueous solubility, the carboxylate salts are protonated with hydrochloric acid to give the free carboxylic acids 24, which may be more desirable for formulation purposes. The synthetic approach of FIG. 17 is compatible with all combinations of sulfur and selenium as the core heteroatoms and with a wider range of aryl substituents than the direct sulfonation approach of FIG. 16. Initial derivatives to be prepared include various amino substituents, trifluoromethyl derivatives, and alkyl chains of varying lengths as indicated in FIG. 17.

Other carboxylic acid derivatives will be prepared that place the carboxyl group directly on the aryl substituent. The addition of disodium sulfide to ☐-bromo 4-bromoacetophenone gives bisketosulfide 25, which can be condensed with glyoxal to give thiophene 26 in 70% overall yield. Reduction of the deketone to the corresponding diol with sodium borohydride gives a diol derivative that can be condensed with pyrrole to give dipyrromethane derivative 19a in 65% yield. Condensation of 19a with various diols 18 give 5,10-bis(4-bromophenyl)-15,20-diaryl-21,23-dithiaporphyrins 27. For the derivative with Ar =Ph, we have successfully converted the 4-bromophenyl groups to the corresponding 4-cyanophenyl groups with CuCN in dimethoxyethane (DME) in 45% yield. Either acidic or basic hydrolysis of the cyano groups gives the corresponding carboxylic acid derivatives 28 in greater than 90% yield.

Figure 18:
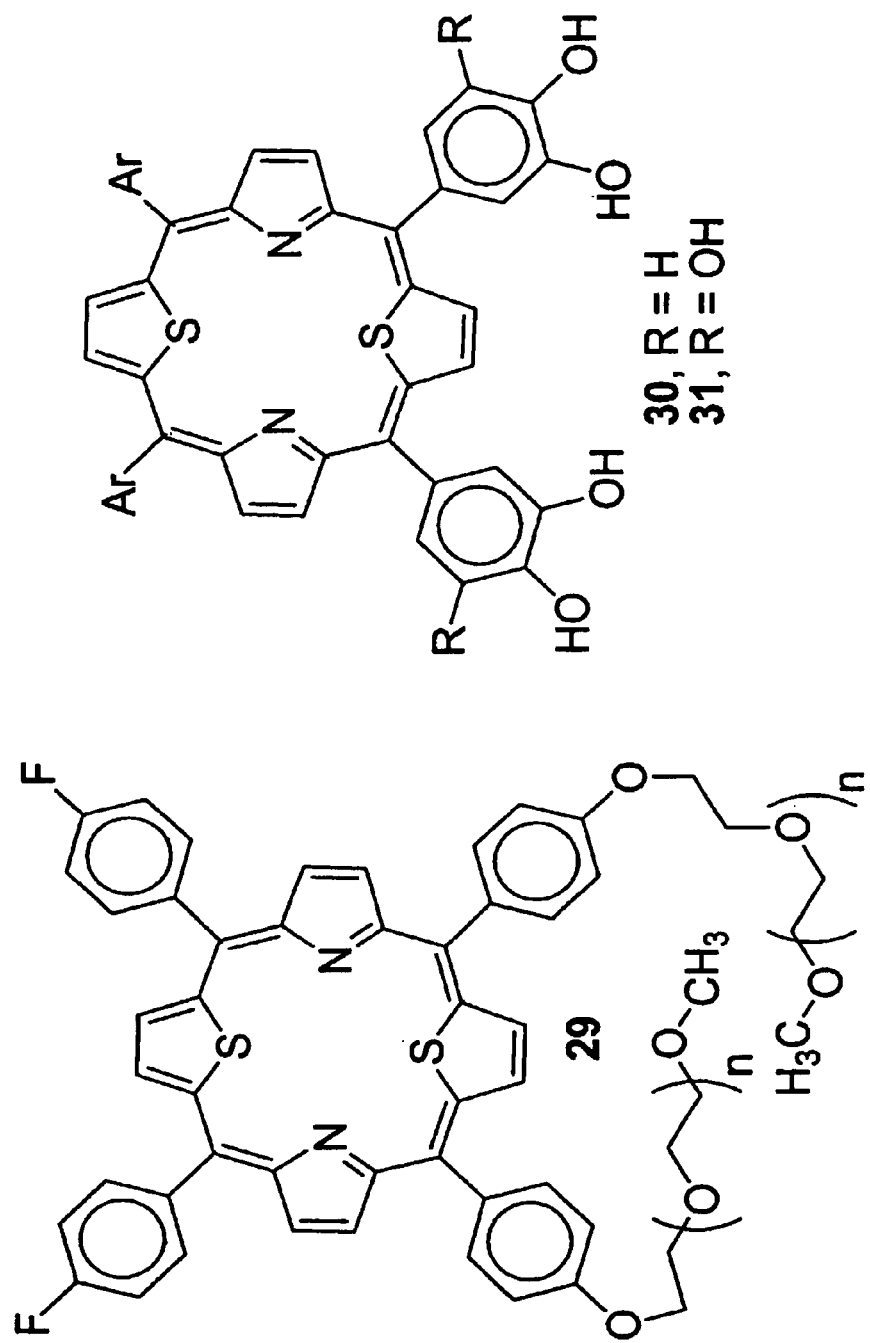
FIG. 18 illustrates the synthesis of PEGylated core-modified prophyrins.

PEGylated derivatives are easily prepared from phenolic derivatives such as 23. Treating 23 (X =F) with sodium hydride in tetrahydrofuran generates the bisphenoxide salt, which can then be alkylated with a commercially available bromoethyl polyethylene glycol oligomer to give core-modified porphyrin 29 in 83% isolated yield as shown in FIG. 18. The oligomers can be selected for varying numbers of ethylene glycol repeat units terminating in the bromoethyl group.

Counter Ion Changes.

With the sulfonate and carboxylate salts, the sodium cations can be replaced with other ions to fine-tune solubility and lipophilicity. In particular, ammonium and various alkyl- (n-octylammonium), dialkyl-(dihexylammonium), trialkyl- (tri-n-butylammonium), and tetraalkylammonium (tetramethylammonium, tetra-n-butylammonium, trimethyl-n-dodecylammonium) salts of the core-modified porphyrins can be prepared using ion-exchange techniques to optimize photosensitizer pharmacokinetics.

Metal-binding Substituents.

Figure 19:
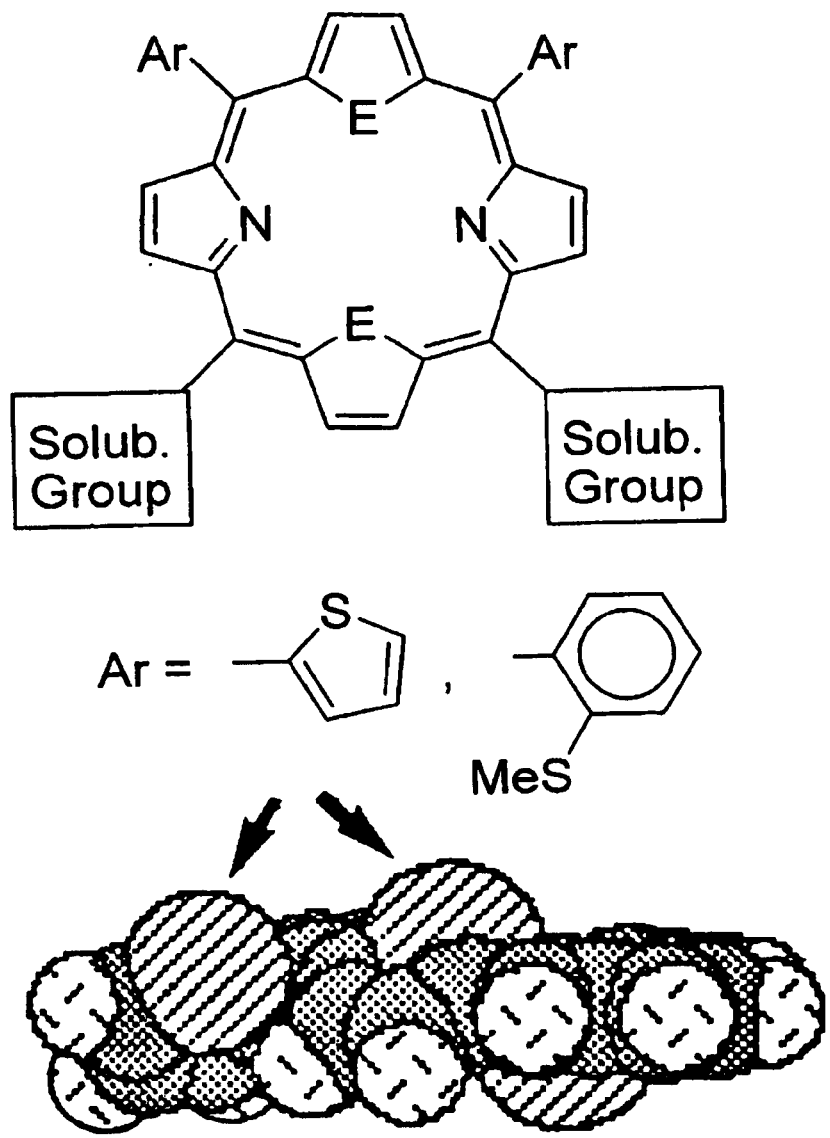
FIG. 19 illustrates 21, 23-core-modified porphyrins with chelating sulfur containing substituents.
Figure 20:
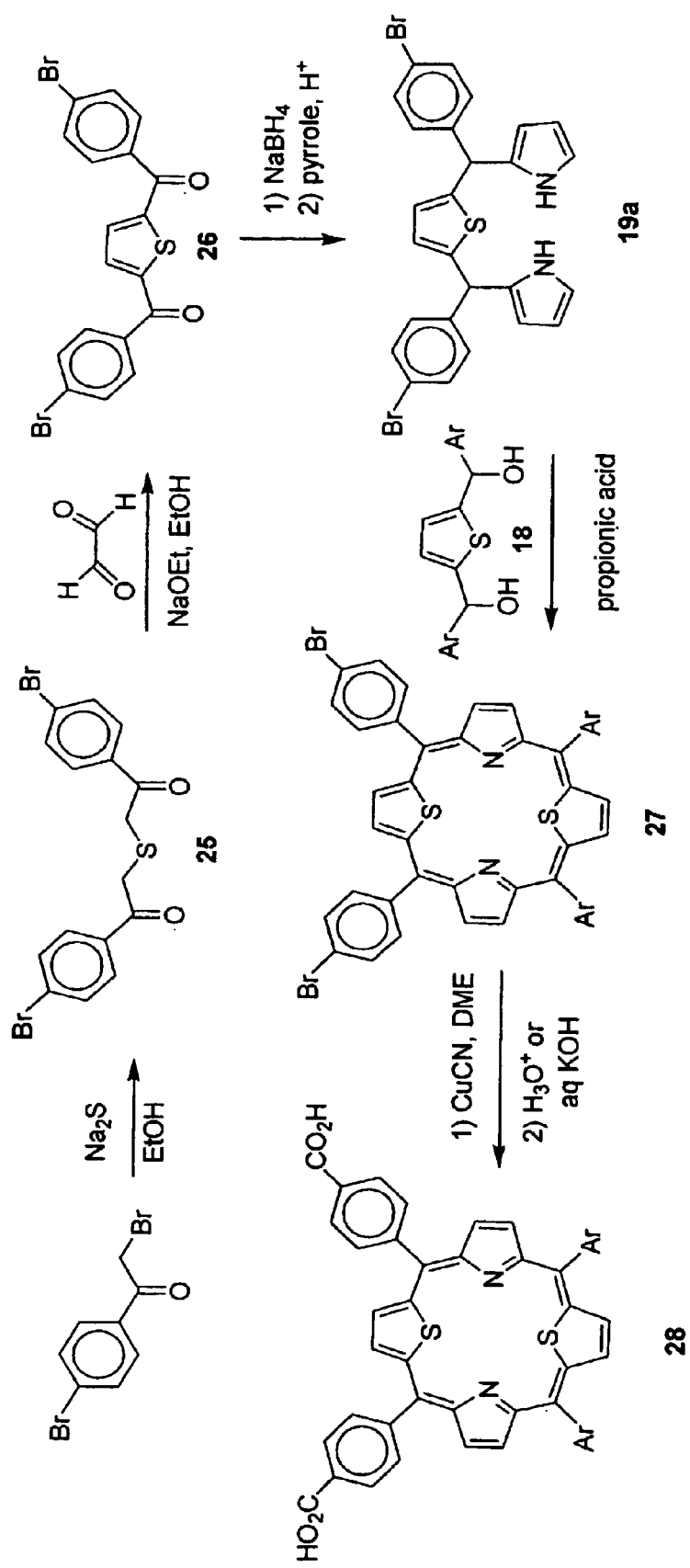
FIG. 20 illustrates preparation of arylcarboxylate derivatives.

Unlike porphyrin derivatives, the 21,23-core-modified porphyrins cannot bind a metal within the core due to the size of the heteroatoms. Metal complexes can be formed if the metal sets on top of the core. Furthermore, the sulfur and selenium heteroatoms are "soft" relative to the nitrogen atoms of the conventional porphyrin core and would have different binding constants. We chose substituents to augment this feature by providing sulfur-containing ligands attached to the core that are capable of chelating a metal bound to a core heteroatom. Our approach is shown in FIG. 19. The meso-2-thienyl substituent can be introduced synthetically using thiophene 2-carboxaldehyde as a starting material in the synthesis of diols 18 (FIG. 16). Similarly, 2-methylthiobenzaldehyde as a starting material would introduce a meso-2-methylthiophenyl substituent. In the 2-thienyl substituted derivatives, the substituent sulfur atom and a heteroatom of the core are located 1,5 to one another and can form a six-membered chelate to a metal atom/ion. This is illustrated in the MM2-minimized space-filling model in FIG. 19 of 5-(2-thienyl)-21,23-dithiaporphyrin. In the space-filling model of FIG. 19, the porphyrin is viewed edge on. The puckering of the core is clearly seen and the heteroatom of the core and the sulfur atom of the substituent can project into the same face of the core-modified porphyrin (as noted by the arrows). The 2-methylthiophenyl substituent places the sulfur of the substituent and the heteroatom of the core 1,6 to one another and can form a seven-membered chelate to a metal atom/ion.

We claim:

1. A photosensitive compound of the formula:

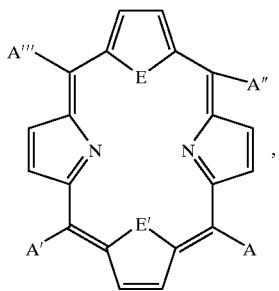

wherein;

A and A' are

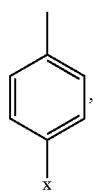

wherein X is H, F or $NME_2$;
E is selected from the group consisting of S, Se, and Te;
E' is selected from the group consisting of S, Se, and Te;
A" and A''' are

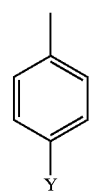

wherein Y is $SO_3$ or $OCH_2CO_2$.

2. A method of providing photodynamic therapy to a patient having at least one tumor comprising the steps of:
administering the compound of claim 1 in a pharmaceutically acceptable carrier to the patient;
waiting for a sufficient time to allow the administered compound to be taken up by a target tissue having the at least one tumor; and
irradiating a region of the patient containing the target tissue, wherein growth of the tumor is inhibited.

3. The method of claim 2, wherein the compound is administered at a dose of about 0.5 to 5.0 $\mu$mol/kg.

4. A method of providing photodynamic therapy to a patient having at least one tumor comprising the steps of:
administering the compound of claim 1 in a pharmaceutically acceptable carrier to the patient;
waiting for a sufficient time to allow the administered compound to be taken up by a target tissue having the at least one tumor; and
irradiating a region of the patient containing the target tissue, wherein growth of the tumor is inhibited.

5. The method of claim 4, wherein the compound is administered at a dose of about 0.5 to 5.0 $\mu$mol/kg.

6. The compound of claim 1, wherein the variable of X of groups A and A' is F and the variable of Y of groups A" and A''' is $SO_3^-$.

7. The compound of claim 1, wherein the variable of X of groups A and A' is F and the variable of Y of groups A" and A''' is $CH_2CO_2^-$.

8. The compound of claim 1, wherein the variable of X of groups A and A' is $NMe_2$ and the variable of Y of groups A" and A''' is $SO_3^-$.

9. The compound of claim 1, wherein the variable of X of groups A and A' is $NMe_2$ and the variable of Y of groups A" and A''' is $CH_2CO_2^{31}$.

10. A photosensitive compound of the formula:

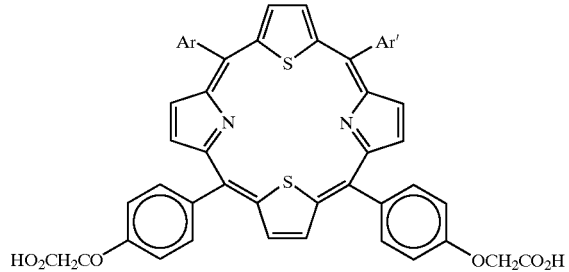

wherein Ar is selected from the group consisting of Ph, 4-$FC_6H_4$, 4-$MeC_6H_4$, and 2-thienyl; and Ar' is selected from the group consisting of Ph, 4-$FC_6H_4$, 4-$MeC_6H_4$, 4-$EtC_6H_4$, and 4-n-$BuC_6H_4$.

11. A method of providing photodynamic therapy to a patient having at least one tumor comprising the steps of:
administering the compound of claim 10 in a pharmaceutically acceptable carrier to the patient;
waiting for a sufficient time to allow the administered compound to be taken up by a target tissue having the at least one tumor; and
irradiating a region of the patient containing the target tissue, wherein growth of the tumor is inhibited.

12. The method of claim 11, wherein the compound is administered at a dose of about 0.5 to 5.0 $\mu$mol/kg.

13. A compound as in claim 10 wherein Ar is 2-thienyl.

14. A method of providing photodynamic therapy to a patient in need thereof, the method comprising:
administering to the patient in a pharmaceutically acceptable delivery vehicle a photodynamic therapy therapeutic dose of a compound with the following structure:

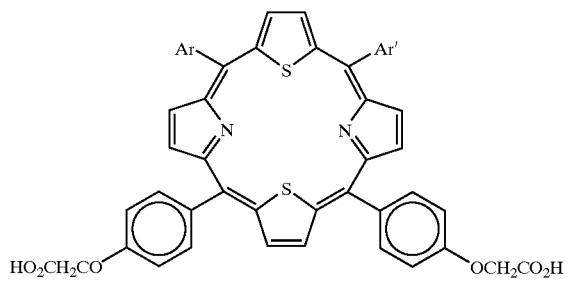

wherein Ar is selected from the group consisting of Ph, 4-FC$_6$H$_4$, 4-MeC$_6$H$_4$, and 2-thienyl; and Ar' is selected from the group consisting of Ph, 4-FC$_6$H$_4$, 4-MeC$_6$H$_4$, 4-EtC$_6$H$_4$, and 4-n-BuC$_6$H$_4$;

waiting a sufficient time to allow the administered compound to be taken up and retained in at least one target tissue; and irradiating a region of the patient containing the target tissue.

15. A method as in claim 14 wherein Ar is 2-thienyl.

* * * * *